United States Patent
Bousfield et al.

(10) Patent No.: US 7,194,316 B2
(45) Date of Patent: Mar. 20, 2007

(54) HAIR COMB, CIRCUITRY, AND METHOD FOR LASER AND GALVANIC SCALP TREATMENT

(75) Inventors: Patrick Bousfield, Middlesex (GB); Mark Chandler, Southern Pines, NC (US); Sanny Chiu, Hong Kong (HK)

(73) Assignee: Elysee Beauty Products, Ltd., Hong Kong (HK)

( * ) Notice: Subject to any disclaimer, the term of this patent is extended or adjusted under 35 U.S.C. 154(b) by 185 days.

(21) Appl. No.: 10/841,616

(22) Filed: May 7, 2004

(65) Prior Publication Data

US 2005/0251242 A1 Nov. 10, 2005

(51) Int. Cl.
*A61N 1/00* (2006.01)
*A61N 5/06* (2006.01)
*A61C 1/00* (2006.01)
*A61B 18/18* (2006.01)

(52) U.S. Cl. .................. 607/150; 607/50; 607/75; 607/89; 607/139; 433/29; 606/9; 606/43

(58) Field of Classification Search ............ 607/50, 607/75, 89, 139, 145, 150; 132/219; 128/422; 433/29; 606/9, 43
See application file for complete search history.

(56) References Cited

U.S. PATENT DOCUMENTS

| | | | | |
|---|---|---|---|---|
| 1,948,990 | A | * | 2/1934 | Mitlehner ............... 607/79 |
| 2,397,757 | A | | 4/1946 | Schwedersky |
| 4,314,554 | A | | 2/1982 | Greatbatch |
| 4,653,495 | A | | 3/1987 | Nanaumi |
| 4,665,921 | A | * | 5/1987 | Teranishi et al. ......... 607/75 |
| 4,753,503 | A | * | 6/1988 | Day et al. ............... 359/18 |
| 5,010,896 | A | | 4/1991 | Westbrook |
| 5,030,090 | A | * | 7/1991 | Maeda et al. ............ 433/29 |
| 5,246,019 | A | | 9/1993 | Godfrey |
| 5,306,143 | A | | 4/1994 | Levy |
| 5,569,368 | A | | 10/1996 | Larsky |

(Continued)

FOREIGN PATENT DOCUMENTS

DK 33 36 939 A1 4/1985

(Continued)

OTHER PUBLICATIONS 2001-2002 Lexington International, LLC, "HairMax LaserComb", http://www.lasercomb.net/qna.htm, 17 pages.

(Continued)

*Primary Examiner*—Robert E. Pezzuto
*Assistant Examiner*—Natasha Patel
(74) *Attorney, Agent, or Firm*—Darby & Darby

(57) ABSTRACT

A handheld head treatment device and method for reducing hair loss and stimulating hair growth by supplying current and laser light to a user's head. The device includes a current generator disposed within a housing configured to output a current for passage into the user's head and a laser source and guide means disposed within the housing configured to output and direct respective portions of the laser beam outward from the hair treatment device toward the user's head when the hair treatment device is in use. The method comprises the step of directing a series of different current and laser treatments to a portion of the scalp wherein the programmed current treatments are sequentially administered and include a continuous and pulsed direct current treatment.

20 Claims, 20 Drawing Sheets

U.S. PATENT DOCUMENTS

| | | | |
|---|---|---|---|
| 5,616,140 A | | 4/1997 | Prescott |
| 5,725,600 A | | 3/1998 | Caisey et al. |
| 5,803,093 A | | 9/1998 | Romano |
| 5,935,156 A | | 8/1999 | Chandler et al. |
| 5,967,967 A | * | 10/1999 | Guo .............................. 600/9 |
| 5,979,454 A | | 11/1999 | Anvari et al. |
| 6,007,502 A | | 12/1999 | Lee |
| 6,026,828 A | * | 2/2000 | Altshuler .................... 132/311 |
| 6,053,180 A | | 4/2000 | Kwan |
| 6,063,108 A | | 5/2000 | Salansky |
| 6,119,038 A | | 9/2000 | Cook |
| 6,129,748 A | | 10/2000 | Kamaei |
| 6,436,127 B1 | | 8/2002 | Anderson et al. |
| 6,443,915 B1 | | 9/2002 | Hwang |
| 6,450,941 B1 | | 9/2002 | Larsen |
| 6,497,719 B2 | * | 12/2002 | Pearl et al. ................... 607/89 |
| 2002/0077679 A1 | | 6/2002 | Lo |

FOREIGN PATENT DOCUMENTS

| | | |
|---|---|---|
| DK | 35 11 281 A1 | 4/1986 |
| EP | 0 139 278 B1 | 10/1984 |
| EP | 0 533 863 B1 | 9/1996 |
| GB | 2 214 804 A1 | 9/1989 |
| WO | WO 98/55180 | 12/1998 |
| WO | WO 00/32121 | 6/2000 |
| WO | WO 01/60457 | 8/2001 |

OTHER PUBLICATIONS

U.S. Appl. No. 10/295,487-A1, filed May 22, 2003, Henry Pearl.

1998 Derwent Information, "Cher/Hair Comb- Chernov E I Aug. 1, 1997 1997RU-113311", P24 P33, 2000-011557/01.

Hairmax, "Stressed About Your Hair? Take Control with the Hairmax LaserComb!", Advertisement, www.hairmax.com/nostress.

* cited by examiner

To Light Source

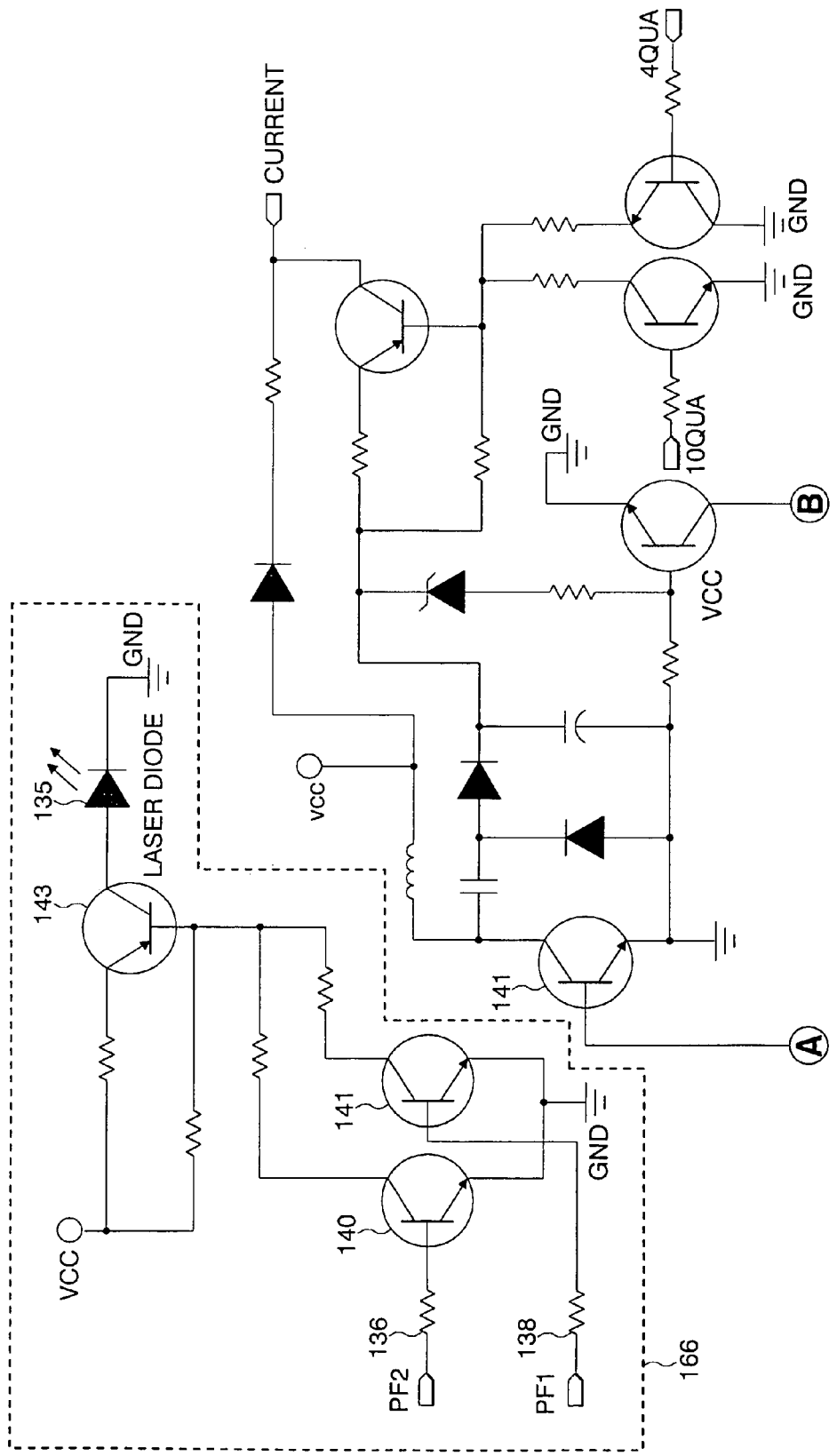
FIG. 11A(1)

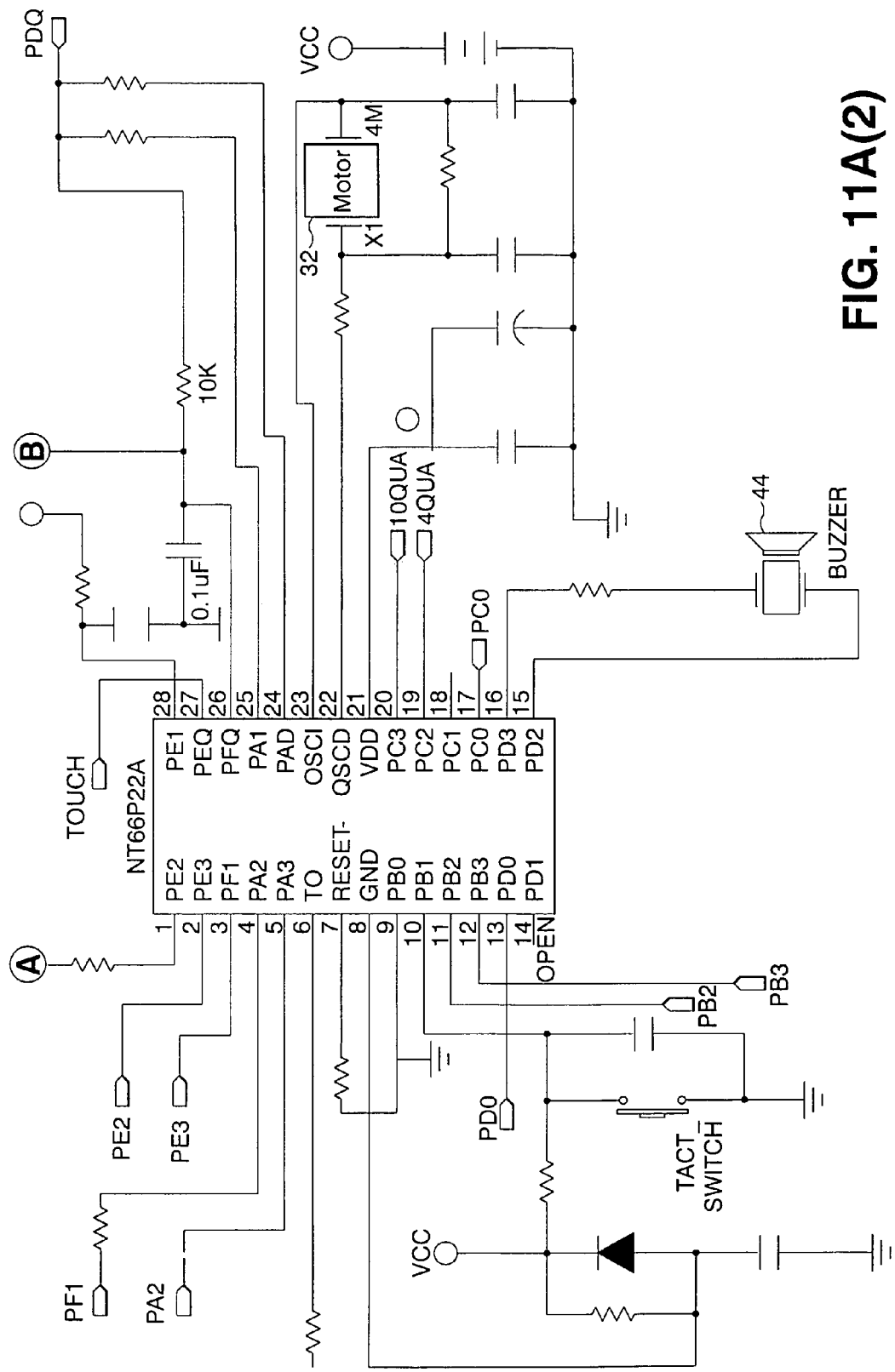
FIG. 11A(2)

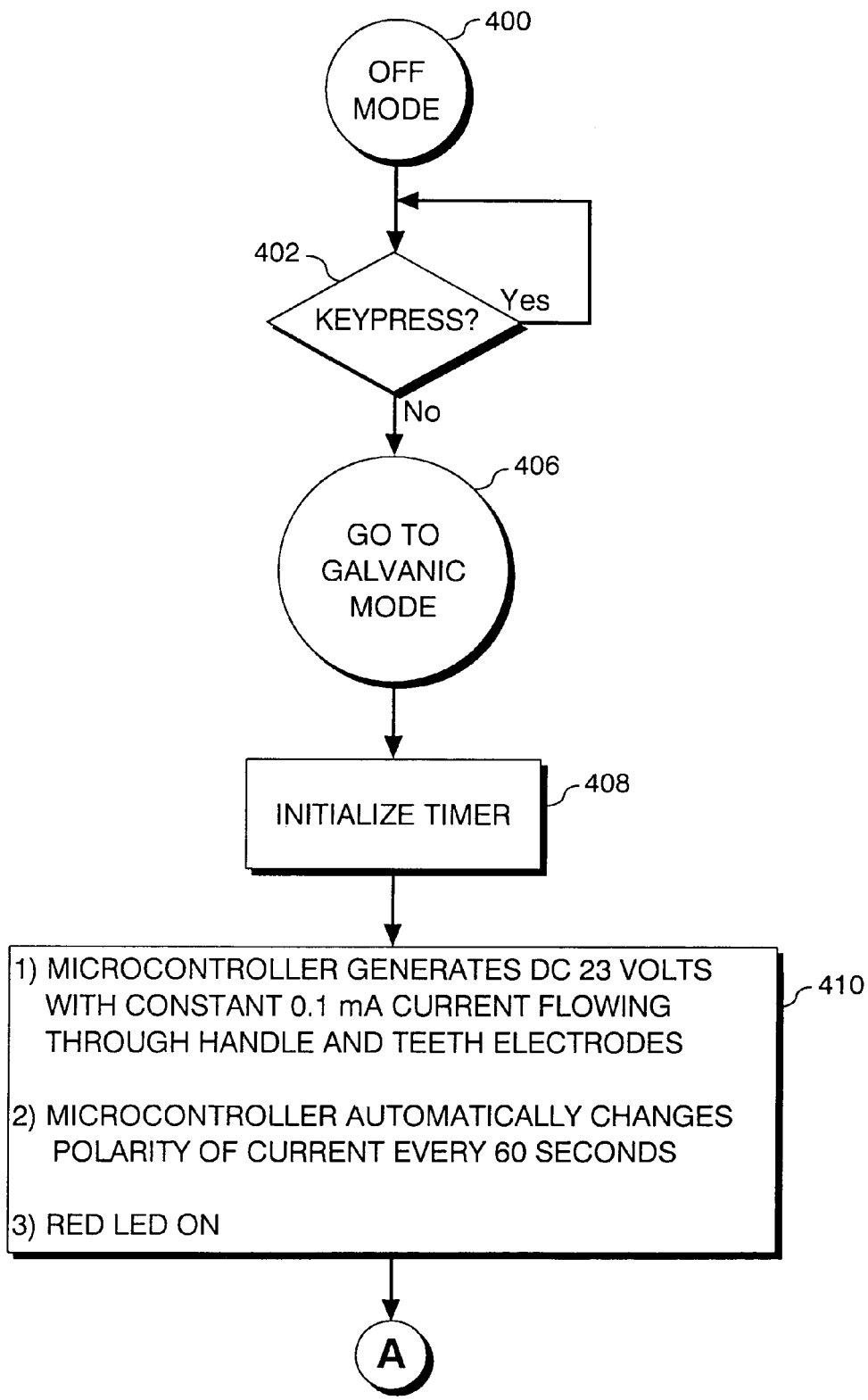
FIG. 12A(1)

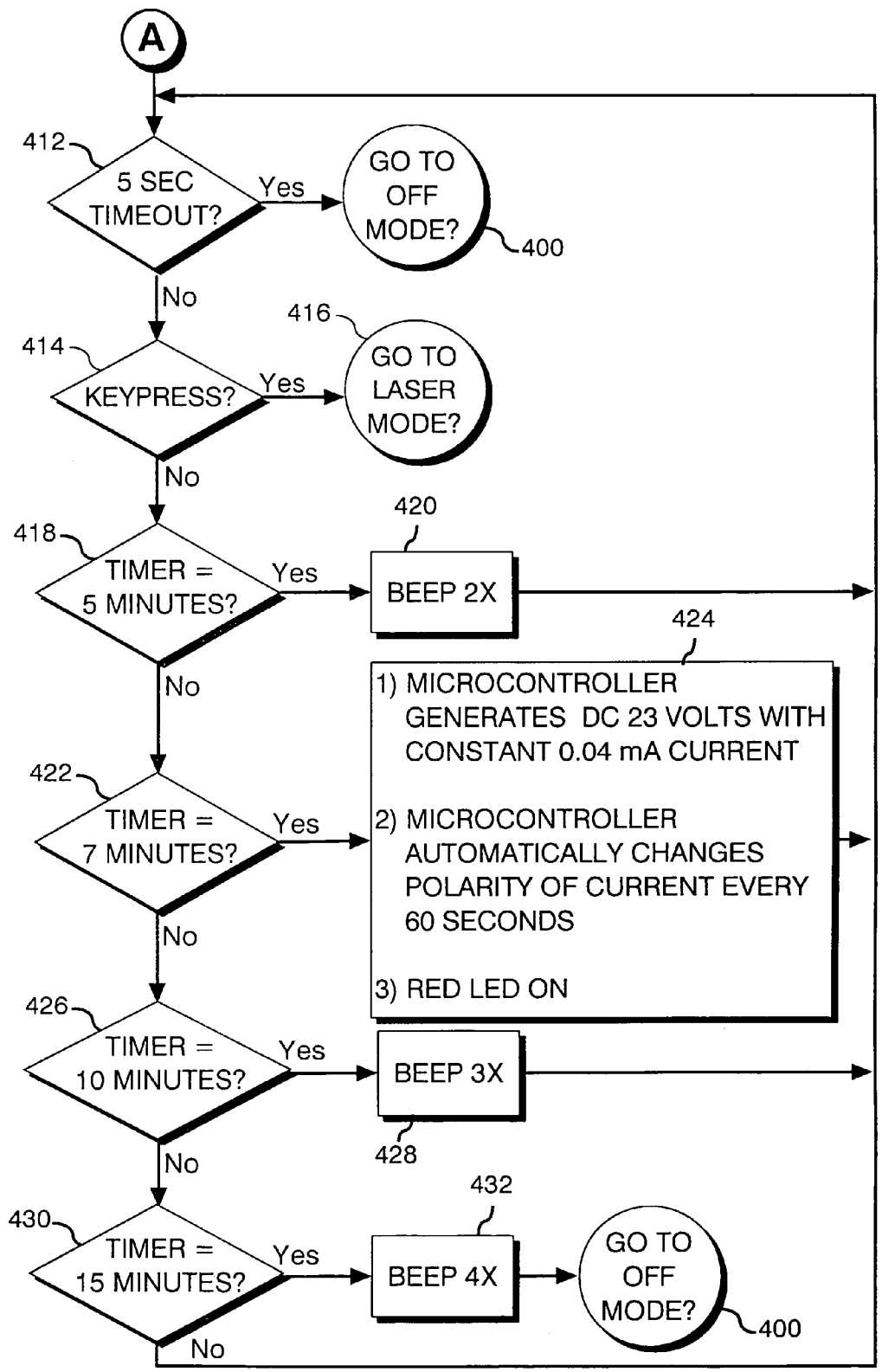
FIG. 12A(2)

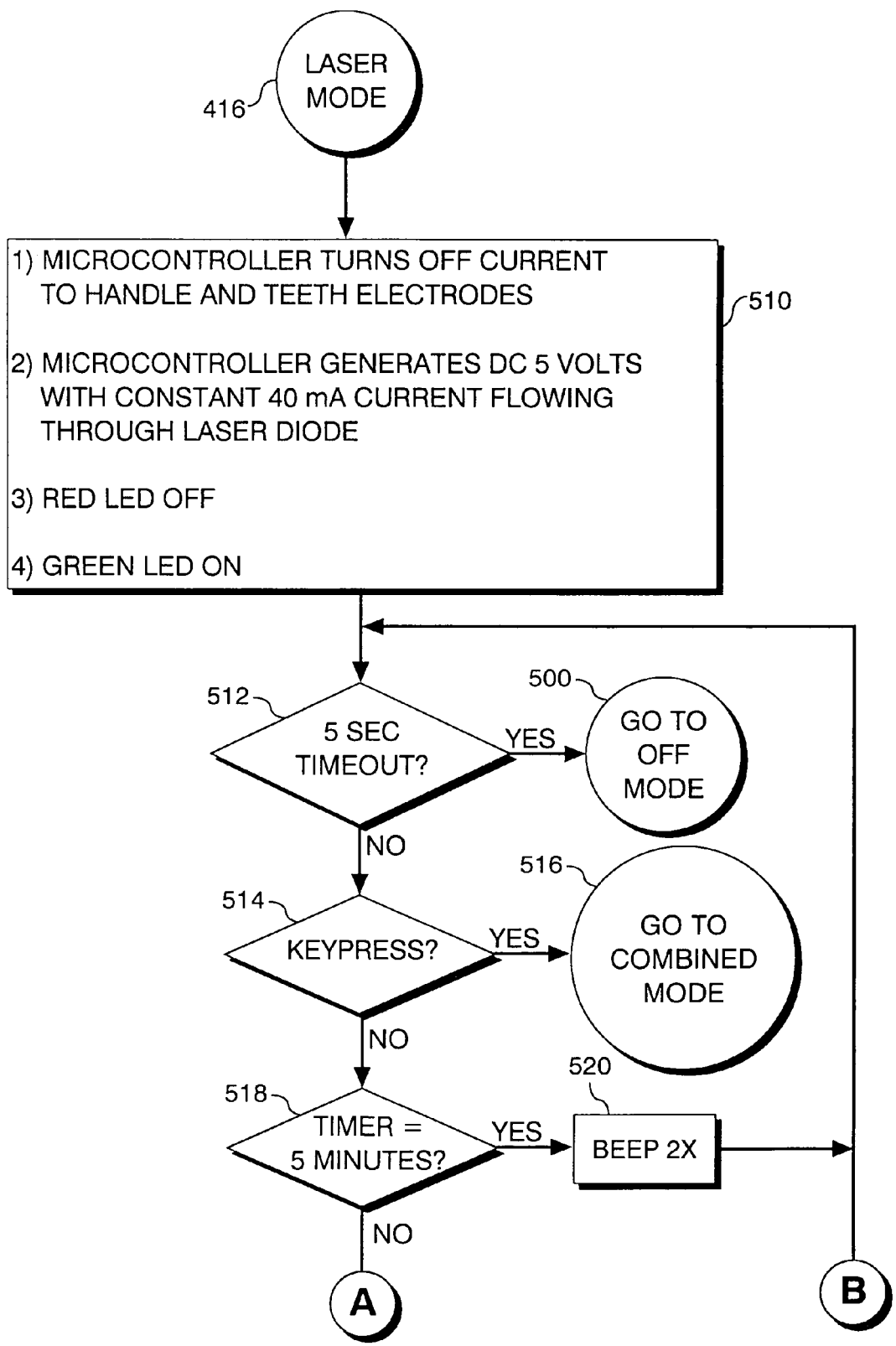
FIG. 12B(1)

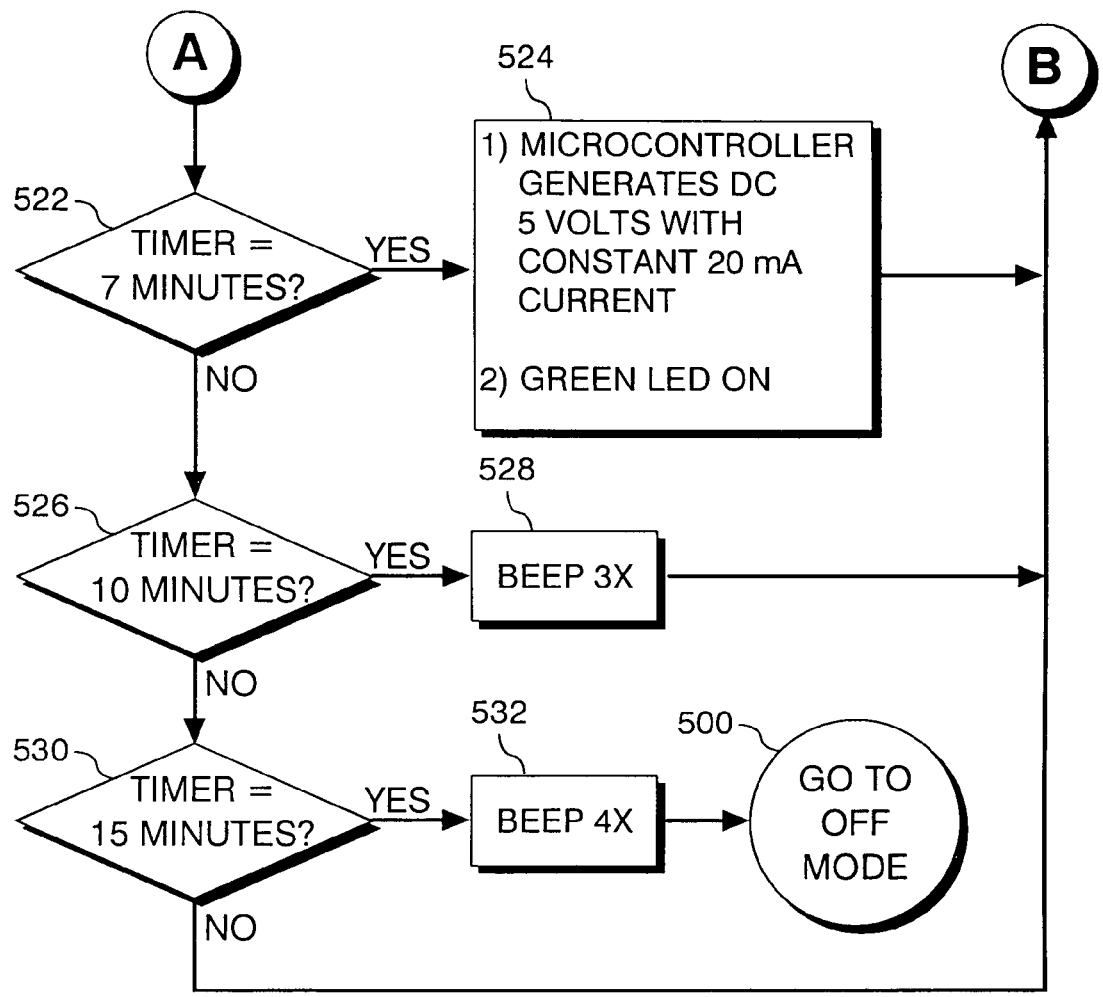
FIG. 12B(2)

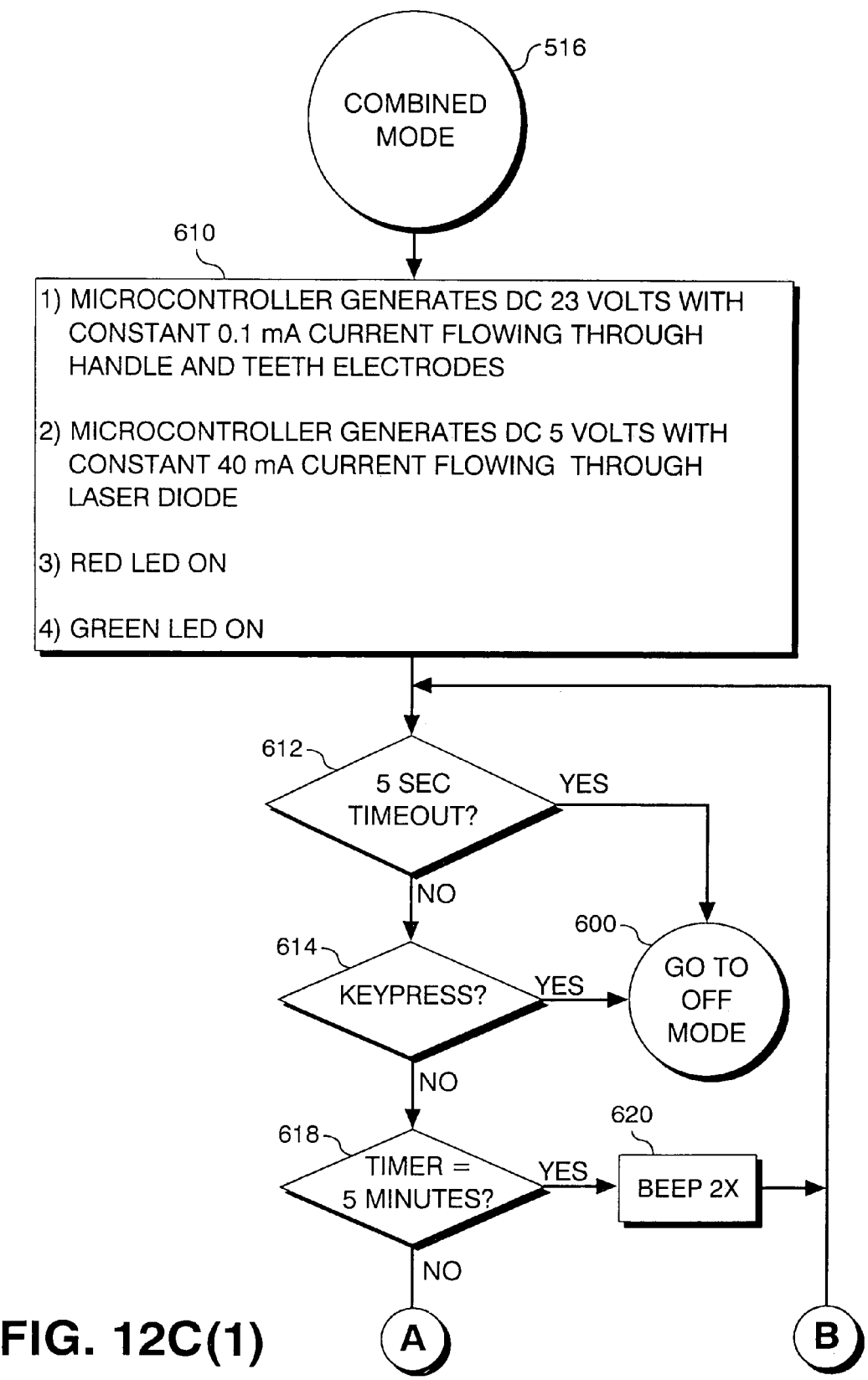
FIG. 12C(1)

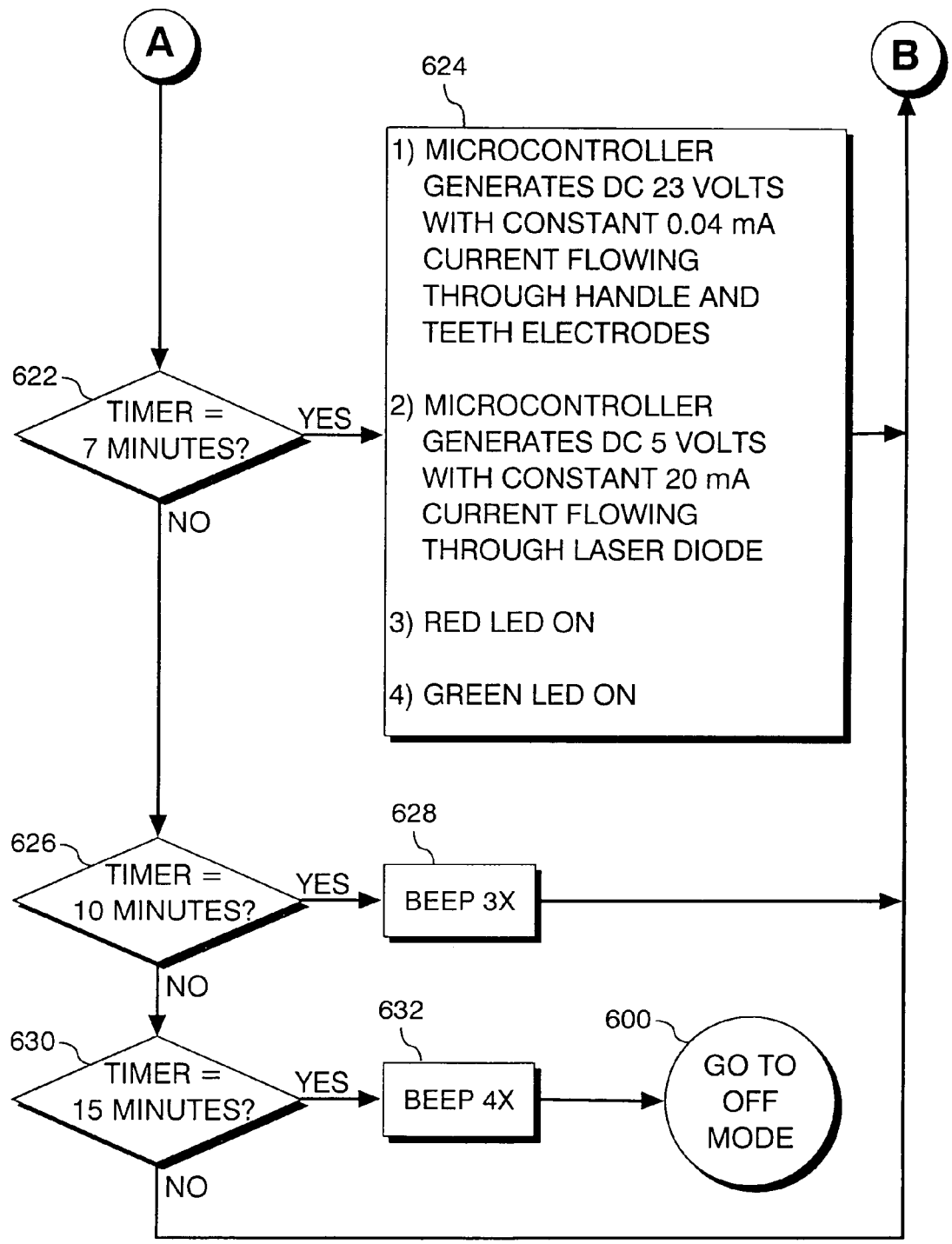
FIG. 12C(2)

HAIR COMB, CIRCUITRY, AND METHOD FOR LASER AND GALVANIC SCALP TREATMENT

FIELD OF THE INVENTION

The present invention relates to a method and apparatus useful in one or more of treating hair loss, treating thinning or damaged hair, and in stimulating hair growth. In particular, it relates to a method and apparatus for treating the scalp or skin of an individual to encourage the healthier growth of hair, and improve the hair's natural condition.

BACKGROUND OF THE INVENTION

The effect of galvanic current treatment on the skin is known. Studies have shown that the application of low-amperage galvanic current on the skin can loosen, open and clean the pores, stimulate the nerves, stimulate protein synthesis and rejuvenate cells. In particular, galvanic current has been said to soften and nourish the skin and increase cellular energy.

Galvanic current is often used today in cosmetology to drive skin treatments deeper into the skin and has been shown to firm and refine skin texture and boost the general health of the skin. The application of galvanic current to an individual's skin has primarily been accomplished with the use of electrical contacts, i.e., electrodes, because of their effectiveness in delivering an even flow of low-amperage galvanic current to the skin.

Several devices for beautifying the skin using galvanic current are known. One such device, described in U.S. Pat. No. 6,443,915 (hereinafter "the '915 patent"), is directed to a portable beautifying apparatus capable of beautifying the human face by selectively supplying far-infrared, galvanic ion current and vibration to the skin of the person's face. The '915 patent uses galvanic current specifically to stimulate the skin and accelerate the cellular energy.

Another handheld skin treatment device, described in U.S. Pat. No. 6,119,038 (hereinafter "the '038 patent"), is adapted to apply electrical current to a user's skin. The device includes a first hand-engaging electrode, a second skin treatment electrode, a rechargeable battery, and electrical circuitry including a microcontroller coupled to the electrodes for applying low levels of electricity to the electrodes for skin treatment.

While the benefits of low-amperage galvanic treatments are known, attempts to use galvanic current to stimulate hair growth have not been considered to applicants' knowledge. Prior art devices such as those described in the '915 and '038 patents claim to stimulate and promote blood circulation on a user's skin, however these devices fail to recognize the usefulness of galvanic current for stimulation of the scalp and promotion of healthier, stronger hair growth nor do they suggest a structure suitable for treatment of hair-covered skin such as the scalp.

The '915 and '038 patents do not discuss the applicability of galvanic current to a user's head for the purpose of rejuvenating cells, improving the condition of the hair follicle and papilla, and increasing energy production and the flow of beneficial nutrients to a user's hair. Nor do they teach application of these portable devices to a person's scalp.

On the other hand, low-power laser light has been applied to the scalp to enhance the physiological state of the scalp and encourage hair growth. One such laser device, described in U.S. Pat. No. 6,497,719 (hereinafter "the '719 patent"), is directed to a handheld comb which emits a row of lasers between parallel rows of teeth extending from the comb body. The lasers, when applied to a user's scalp, are said to increase scalp blood circulation resulting in the scalp, and the hair follicles, receiving a more abundant supply of nutrients from the body. The use of laser light, as disclosed in the '719 patent, is said to encourage hair growth. However that device has several significant drawbacks which the present invention overcomes. For example, there is a limit on the amount of laser power that can be applied to a person's scalp before the benefits of the laser treatment are outweighed by more harmful conditions, such as scalp redness, dryness and peeling. Accordingly, the strength of the lasers used in the '719 patent must be constrained to a reasonably safe value to prevent possible injury to the scalp and hair. It would be beneficial to be able to provide a user with a more effective hair treatment device without subjecting the person to increased radiation from a more powerful laser output.

Further, it would be an improvement in the art to provide such a device which includes user control over which treatment, galvanic current or laser light, is applied at a given moment, effectively allowing a user to switch between a galvanic and laser light treatment, or alternatively, apply a combination of the both of these treatments. It would also be an improvement in the art to provide a hair and scalp treatment device that is programmed to produce in sequence a series of different current waveforms and laser strengths for treatment. The present invention addresses these and other needs in the art.

SUMMARY OF THE INVENTION

The invention described herein provides an improvement over prior-art hair and scalp treatment methods and devices. The present invention is a handheld head treatment device for reducing hair loss and stimulating hair growth by supplying current and laser light to a user's head.

According to one aspect of the invention, a handheld treatment device for use with a user's head comprises a housing with a handle portion and a head portion, a current generator disposed within the housing configured to output a current for passage into the user's head, a first conductive surface associated with the handle portion and contactable by a user when the treatment device is being held, a second conductive surface associated with the head portion and contactable with the user's head when the treatment device is in use, and a circuit path defined among the first conductive surface, the second conductive surface and the current generator. When the handle and head portions are simultaneously contacted by the user, the circuit path is in a closed state and the current generator outputs a current substantially less than 1 Ampere.

Optionally, in accordance with a further aspect of the invention, the treatment device can include a control circuit connected to the circuit path which is operative to disable the current output of the current generator in response to interruption of the closed state of the circuit path.

With respect to the method of administering current treatment to a portion of the head and scalp, the method of the present invention comprises the step of sequentially directing to an area being treated a series of different and programmed current treatments wherein the programmed current treatments sequentially administered include both a pulsed direct and continuous direct current treatment.

In accordance with further aspects of the invention that can be included in one or more different embodiments, the treatment device comprises a laser source disposed within the housing configured to output a laser beam and a plurality of optical cables disposed within the housing. Each optical cable can have a first end optically coupled to the laser source so as to convey a portion of the laser beam to a second end of the optical cable. The second ends of the plurality of optical cables can be spaced from one another. The first ends of the optical cables can be orientated so as to receive a portion of the laser beam output by the laser source. The second ends of the optical cables can be oriented so as to direct respective portions of the laser beam outward from the hair treatment device and toward the user's head when the hair treatment device is in use. A retaining member can be provided for retaining the first ends of the optical cables in a position where the ends can receive a portion of the laser beam output by the laser source. At least one of a rigid comb and a bristle brush can extend from the head portion, wherein the second ends of the optical cables are disposed within at least one of the rigid comb and the bristle brush. Multiple ones of these arrangements can be combined in any particular embodiment.

These and further aspects, features and advantages of the present invention will become more apparent from the following description when taken in connection with the accompanying drawings which show, for purposes of illustration only, several embodiments of the present invention.

BRIEF DESCRIPTION OF THE DRAWINGS

FIGS. 11A, 11B and 11C show a circuit diagram with major sections of the circuitry enclosed in dashed-dot blocks;

FIGS. 12A, 12B and 12C show a flow diagram of steps for implementing the galvanic, laser and combined modes of therapy, respectively;

DETAILED DESCRIPTION OF CERTAIN PREFERRED EMBODIMENTS

Figure 1:
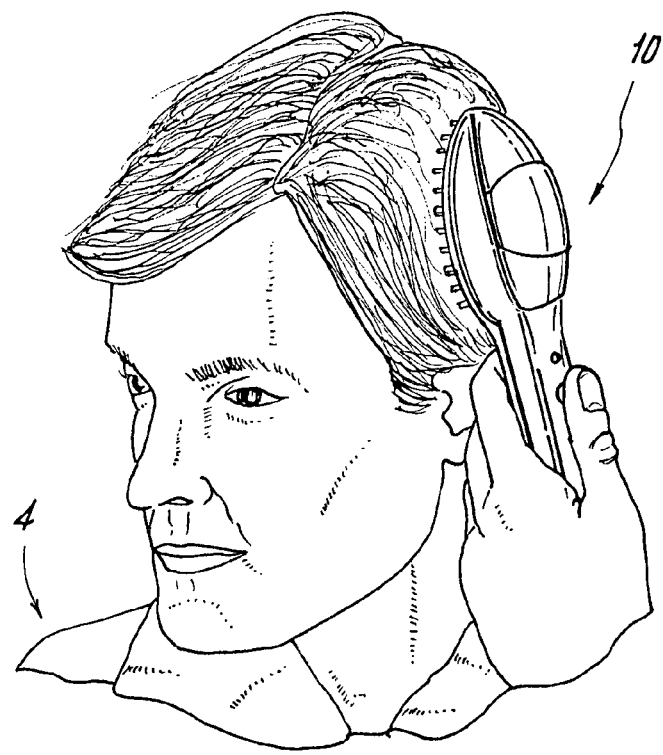
FIG. 1 shows a perspective view of the treatment device in relation to a user's head and hand during treatment.

Referring to FIG. 1, a perspective view of a hair treatment device 10 according to the present invention in which the user 4, grasping the handle of treatment device 10, combs the teeth of device 10 through his hair as he would a conventional comb or brush.

Figure 2:
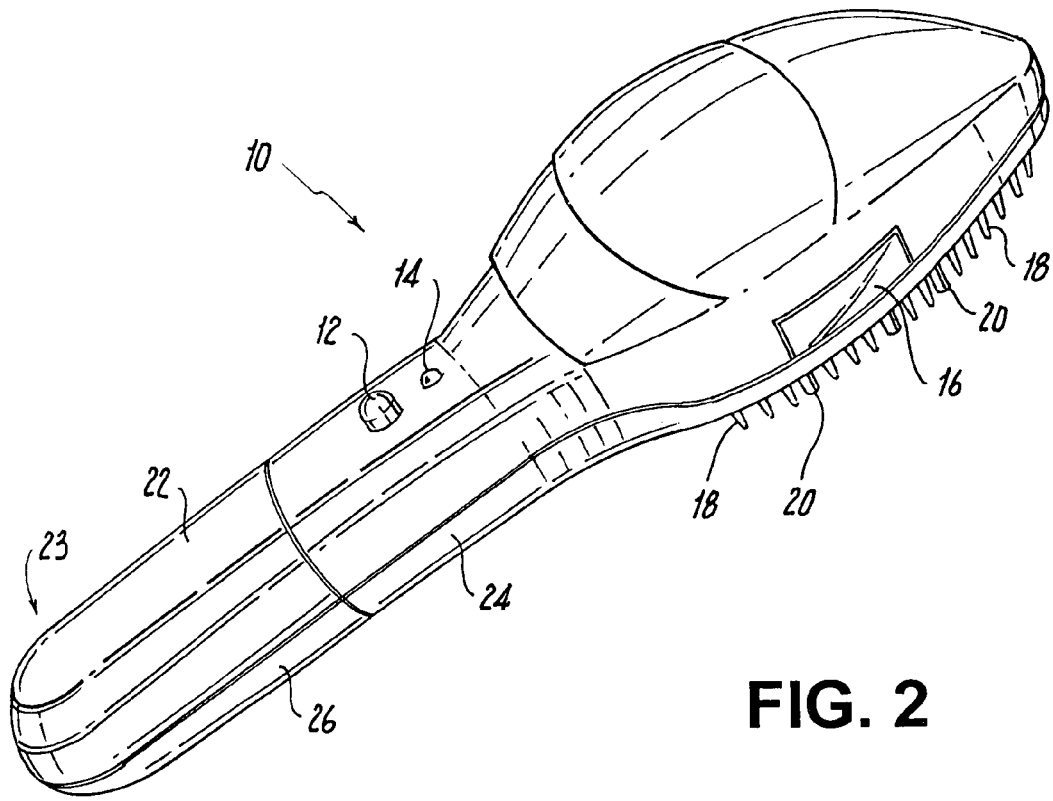
FIG. 2 is a top perspective view of a preferred embodiment of the treatment device which illustrates a control button, an indication window, first and second conductive surfaces and outwardly projecting teeth.

Referring to FIG. 2, a perspective view of the hair treatment device 10 according to a preferred embodiment is shown. FIG. 2 illustrates the external components of the device including respective upper and lower housings, 22 and 24, battery cover 26, teeth 18 for providing galvanic current treatment, teeth 20 for directing laser treatment, and an indication window 16 and light 14 for signaling a user during treatment. Also shown is handle 23 defined by a portion of upper housing 22 and battery cover 26.

Figure 3:
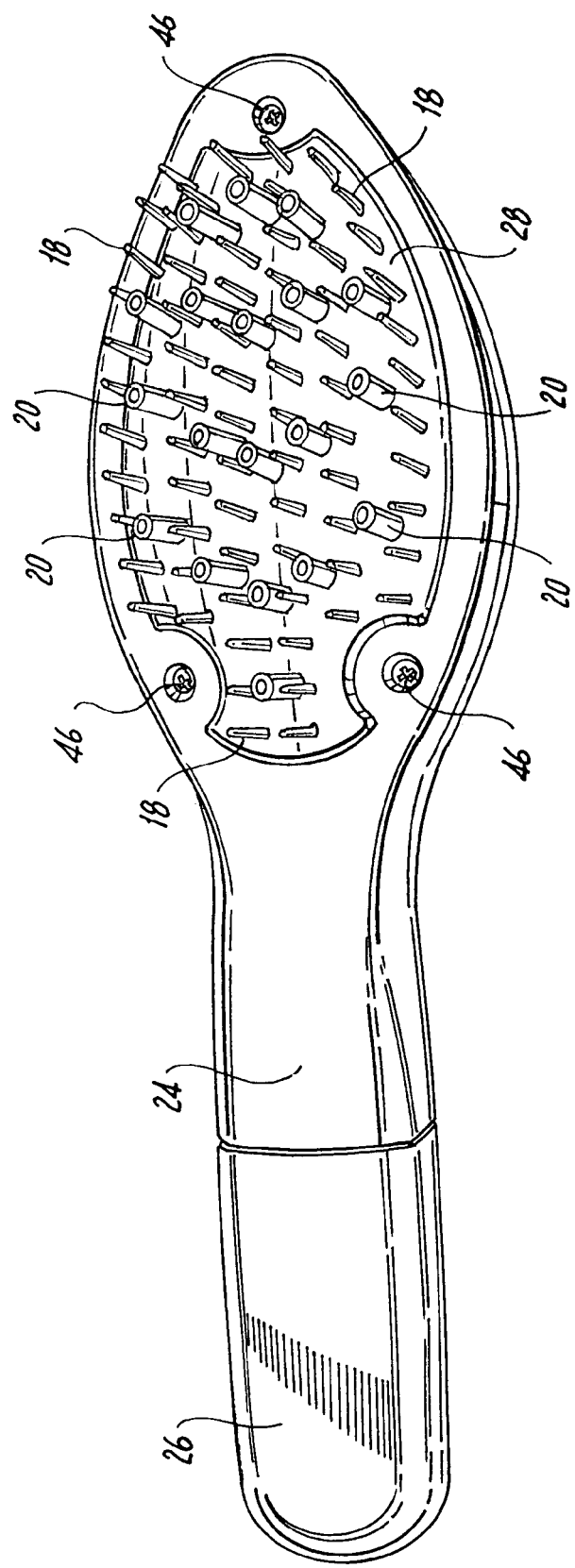
FIG. 3 is a bottom view of the device of FIG. 2.

Referring to FIG. 3, a bottom view of the hair treatment device 10 in which teeth 18 and 20 of FIG. 2 are shown in more detail. Teeth 18 extend from a support assembly 28. Both teeth 18 and support assembly 28 include an exterior conductive surface for conducting current across their surfaces. Thus, current passing over the surface of support assembly 28 can travel over teeth 18 and vise versa. Teeth 20 are each configured with an open-end portion defining a cavity for receiving and housing optics. Unlike teeth 18, teeth 20 project through orifices 68 (FIG. 8) in support assembly 28. Accordingly, current passing over the surface of support assembly 28 and teeth 18 does not travel to teeth 20, unless teeth 20 are also provided with an exterior conductive surface, in which case any portion of teeth 20 in contact with support assembly 28 is also operable to conduct a current. According to the preferred embodiment, teeth 20 are non-conductive and teeth 18 and support assembly 28 are conductive. Thus, teeth 18 can be used to conduct current to the user's head and teeth 20 can be used to direct laser light to the user's head, as described in further detail below. Additionally, while teeth 18 and 20 are shown as rigid comb-like members, flexible bristle members with the same or similar conductive properties can be used with treatment device 10 instead. FIG. 3 also illustrates one possible position for screws 46 for fixedly connecting lower and upper housings 22 and 24 together.

Figure 4:
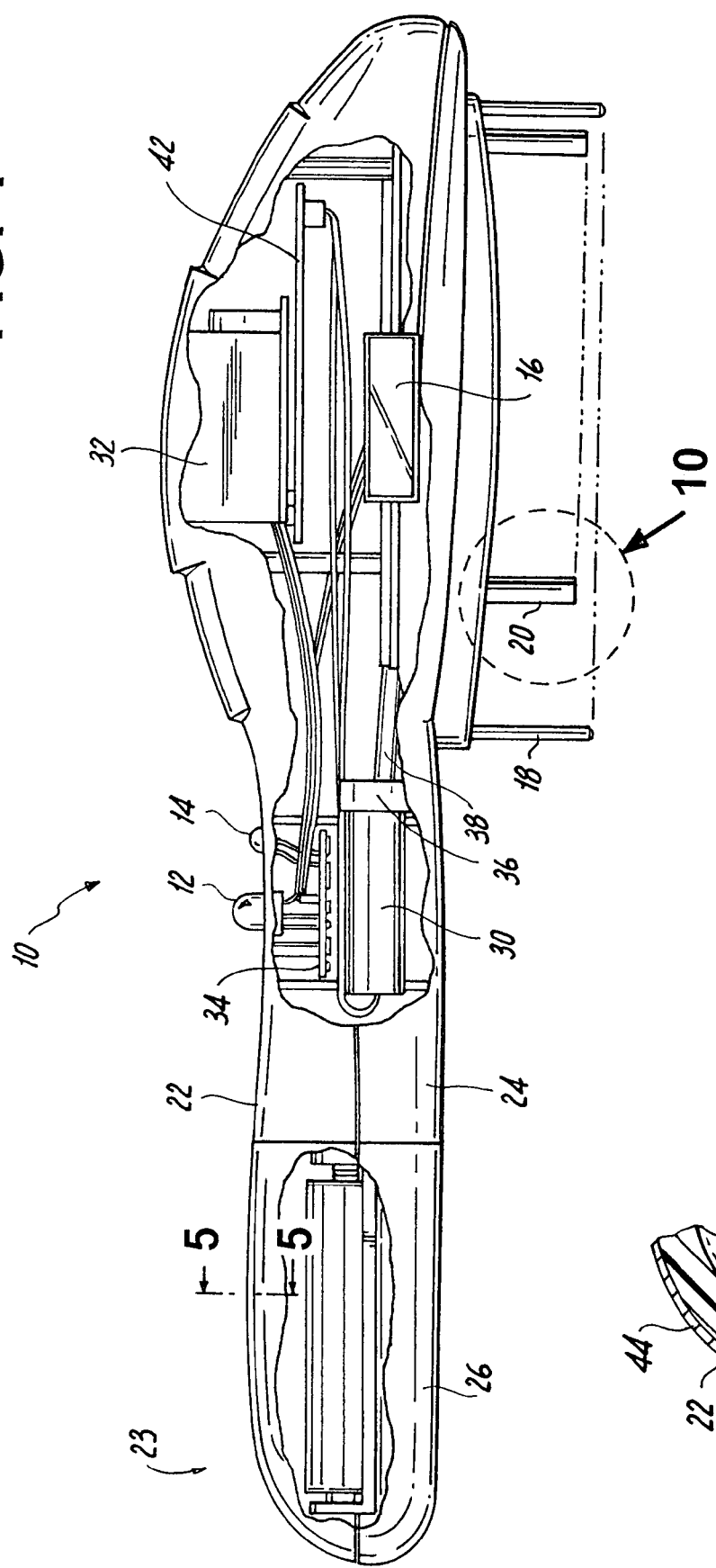
FIG. 4 is a side cutaway view of a preferred embodiment of the device which illustrates an arrangement of components of the device of FIG. 2.

Referring to FIG. 4, a side cutaway view of the preferred embodiment is shown which illustrates the preferred arrangement of several components of the device. Two printed circuit boards, PCBs 34 and 42, are shown for controlling the operation of treatment device 10. Specifically, PCB 34 is connected to a user operable button 12 and an indication light 14 for signaling the user, i.e., when button 12 has been pressed or treatment device 10 has changed modes. PCB 34 is connected to PCB 42 which is provided for controlling a plurality of output devices and treatment modes, such as laser source 30, indication window 16 and resonator 32. An oscillator, e.g., a crystal oscillator, may be used in place of resonator 32. Additionally, PCB 42 is configured to act as a current generating means and output a galvanic current to conductive surfaces of support assembly 28 and handle 23 for passage into the user's head. Preferably this output is no more than about 1 mA, but the device can be configured to output current greater than that (e.g., 1 Ampere) without departing from the teachings of the present invention. However, lower currents in the milliamp range are preferred. It should be appreciated that a single PCB could be used to achieve the wiring described herein.

Figure 5:
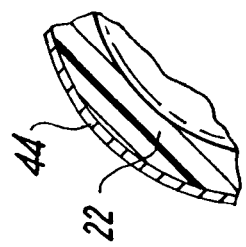
FIG. 5 is a cross-sectional view of a portion of the upper housing of the device taken along the line 5—5 in FIG. 4.

As shown in FIG. 4, handle 23 is defined by a portion of upper housing 22 and battery cover 26. According to the preferred embodiment, the surface of handle 23 includes a conductive layer 44 (FIG. 5) and extends approximately the length of battery cover 26. While conductive layer 44 is shown extending approximately the length of battery cover 26, it may extend further, e.g., to the button 12.

The components of treatment device 10 are held together and supported by lower and upper housings, 24 and 22, respectively. Button 12 is exposed through an orifice in upper housing 22 and provides user control of treatment device 10 including in the preferred embodiment both turning the device on and off and selecting the treatment mode by cycling through the available selections with each button press. Display light 14 and indication window 16, also visible to the user through upper housing 22, are connected to PCB 34 and 42 and can be configured to illuminate in various colors as a function of the number of presses of the button 12, the treatment mode, and/or at predetermined intervals during treatment (e.g., to provide an exciting lighting effect).

Figure 6:
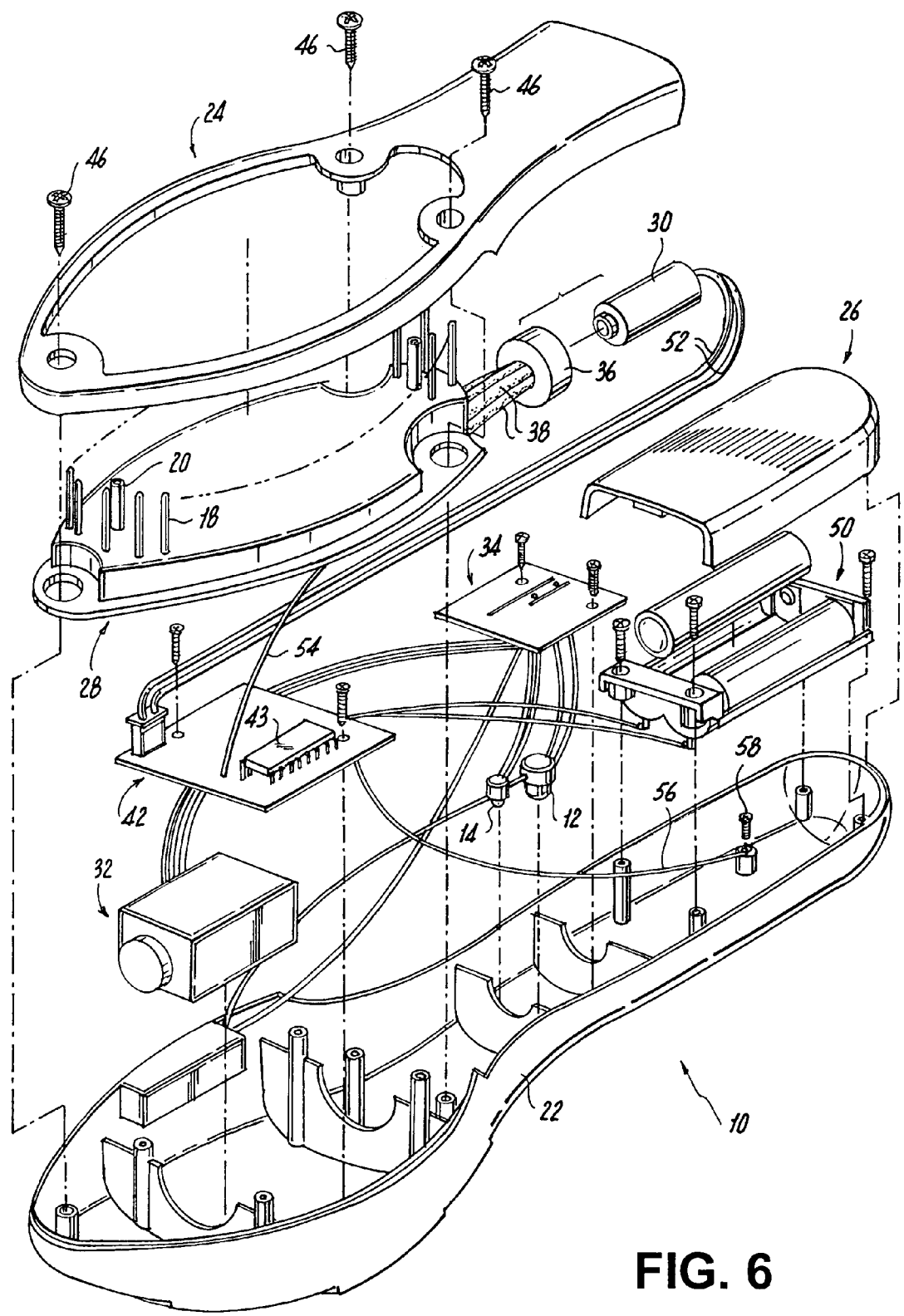
FIG. 6 is an exploded, bottom perspective view of the preferred embodiment of the device.

Referring to FIG. 6, an exploded perspective view of a preferred embodiment is illustrated in which the components of the system can be seen in relation to one another. As shown, PCB 42 is connected to support assembly 28 via wire 54 and to an inner surface of handle 23 via wire 56 for the purpose of conducting current thereto. Wires 54 and 56 are preferably made of copper, however other wires having conductive properties can be used. PCB 42 can selectively supply current to the conductive surfaces of support assembly 28 and handle 23 via wires 54 and 56 according to the control of a microcontroller 43, the operation of which is described in greater detail below. Laser source 30 is connected to PCB 42 via wires 52 and can be controlled by microcontroller 43 through its connection thereto. Also shown in this figure are lower housing 24, upper housing 22, teeth 18 and 20, user operable button 12, battery unit 50 and associated hardware such as screws 46 and 47 for joining and securing the components of treatment device 10 to upper and lower housing 22 and 24, respectively. The battery unit 50 may be implemented by the use of two commercially available AA size batteries for example. According to an alternative arrangement treatment device 10 may include a rechargeable battery such that device 10 is rechargeable.

Figure 8:
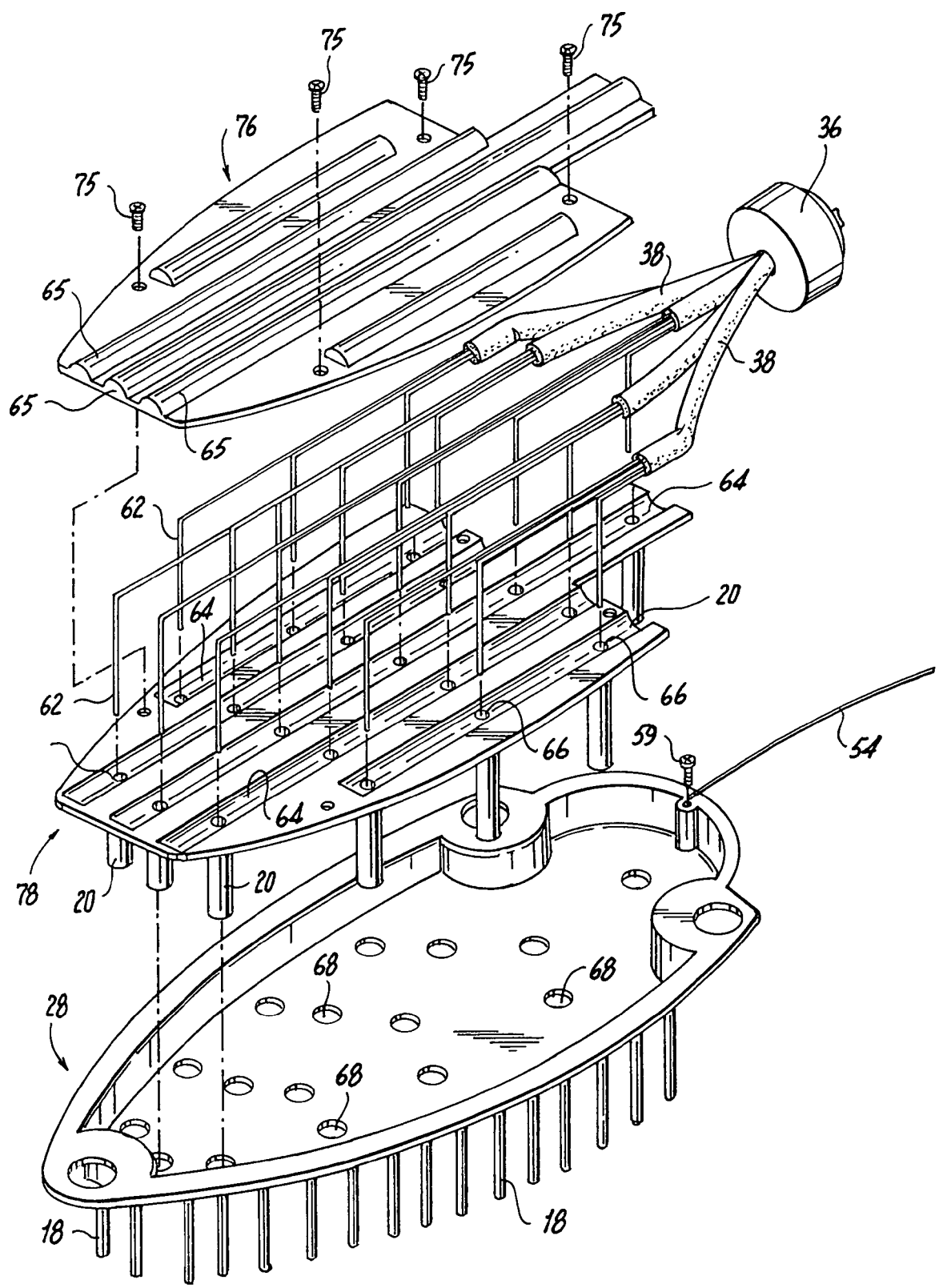
FIG. 8 is an exploded view of an arrangement of optical cables and the relationship between the cables, the guide aperture and the support assembly.

Wires 54 and 56 conduct current between PCB 42, support assembly 28 and handle 23. As shown, wire 56 can be secured to a conductive underside of upper housing 22 by screw 58. To ensure that current conducts throughout handle 23 the conductive threads of wire 56 must remain in constant contact with the conductive underside of upper housing 22. The same condition must also be met for wire 54 and support assembly 28. Persons of skill in the art will appreciate that wires 54, 56 can be conductively connected in other ways; What is important is that an electrical connection be established between these wires, the support assembly, and the handle. While covered from view in FIG. 6, wire 54 can be attached to a conductive surface of support assembly 28 via screw 59, as shown in FIG. 8. As mentioned above, the surfaces of support assembly 28, teeth 18 and handle 23 are preferably coated with a metallic-conductive paint, such that current supplied to wires 54 and 56 can travel over the undersurface of assembly 28 and handle 23 to the outer surfaces where contact can be made with the user's hand and head. Accordingly, although wire 56 is connected internally to treatment device 10, the continuity of the conductive surface between the inner and outer surfaces of the housing allows current to flow from wire 56 over the underside of handle 23 to the outer surface contactable by the user. In the course of actual electrical treatment, an electrical circuit is established from PCB 42 to teeth 18 (which are moved over and on the scalp or through the hair), through the body of the user, back to the treatment device 10 through handle 23 and from the handle 23 back to PCB 42. Contact with the scalp by a portion of the teeth 18 improves conductivity in the electrical circuit so-established.

Figure 7:
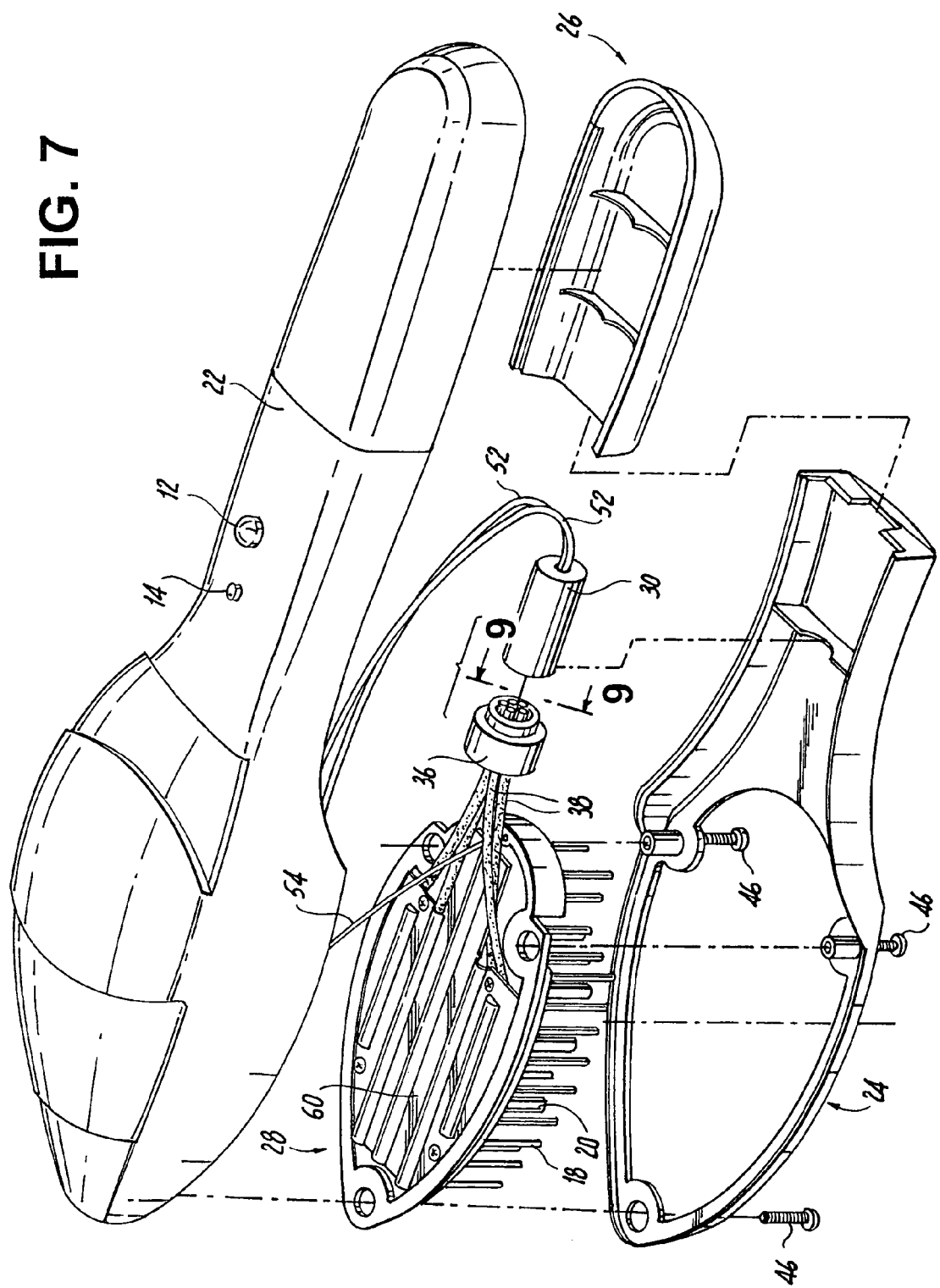
FIG. 7 is an exploded, top perspective view of the device which illustrates more particularly the arrangement of a laser source, guide aperture and support assembly.

Referring to FIG. 7, another exploded perspective view of the preferred embodiment is illustrated. Several components have been eliminated from this figure which is intended to show the relative position of the laser source 30, guide cables 38, guide aperture 60 and coupling assembly 36 in relation to upper and lower housings, 22 and 24, respectively. Guide cables 38 each house a plurality of optical cables 62 (FIG. 8) which are configured to convey a portion of the output of laser source 30 through teeth 20 to the user's head. Coupling assembly 36 engages the first ends of guide cables 38, preferably encircling, securing and aligning the first ends with the laser output of laser source 30.

Coupling assembly 36 provides mechanical alignment of guide cables 38 with laser generator 30 while substantially enhancing the ease of manufacture by allowing parts to be interchangeable, e.g., laser source 30. Second ends of guide cables 38 terminate at or near a marginal edge of a guide aperture 60. Guide aperture 60 is configured to fit securely with support assembly 28, and the support assembly is held securely within the device between upper and lower housings, 22 and 24, respectively. Orifices provided in the support assembly and lower housing can be aligned and are configured for accepting screws 46 which secure support assembly 28 with lower housing 24 and upper housing 22. Referring to FIG. 8, guide aperture 60 comprises a lower and upper housing, 78 and 76 respectively. The second ends of guide cables 38 terminate in alignment with guide grooves 64, exposing optical cables 62 thereto, and aligning them with each respective guide groove 64. According to a preferred embodiment, one guide cable 38 is aligned with each guide groove 64 and as shown in FIG. 8, one optical cable 62 is provided for each of tooth 20.

Referring to FIG. 8, a plurality of optical cables 62 extending from each guide cable 38 are aligned to rest in guide grooves 64. As shown, each guide groove 64 is aligned with several teeth 20 and is configured to securely hold and guide a plurality of optical cables 62 into cavities each successive tooth 20 that it is aligned with. Guide grooves 64 include orifices 66 for receiving second ends of optical cables 62. Each orifice 66 is aligned with a tooth 20 such that it defines a port for receiving an optical cable 62 into the respective tooth 20. Accordingly, each optical cable 62 can be bent (e.g., 90°) downward to extend through orifice 66 into hollow tooth 20. Each tooth 20 is configured to receive at least one optical cable 62. According to a preferred embodiment, optical cables 62 are configured of varying lengths such that as they exit guide cable 38, shorter length optical cables 62 can be guided via guide groove 64 into teeth 20 closer to terminating end of the guide cable 38 (where the guide cable 38 meets guide aperture 60) and longer length optical cables can be guided into teeth 20 further away from the terminating end of guide cables 38.

After optical cables 62 are aligned and positioned in guide grooves 64 and second ends of each cable are directed through orifices 68 and into a respective tooth 20, upper housing 76 and lower housing 78 are sealed together. Upper housing 76 includes matching guide grooves 65 which are configured to align with guide grooves 64 of lower housing 78 such that optical cables 62 are securely held in place in cavities formed by guide grooves 64 and 65 when the lower and upper housings are brought together. A plurality of screws, preferably composed of plastic or some other non-conductive material, can be used to secure lower and upper housings, 78 and 76, together.

As discussed above, securing upper housing 78 atop lower housing 78 can secure optical cables 62 in their respective guide grooves 64, 65 and teeth 20. The bends in optical cables 62 prevent the cables from slideably moving in the guide grooves. Once lower and upper housings 78 and 76 are secured, teeth 20 of lower housing 78 are aligned with orifices 68 of support assembly 28. Once aligned, support assembly 28 and guide aperture 60 can engage each other with teeth 20 extending through orifices 68. Orifices 68 are large enough to accommodate teeth 20 and, according to the preferred embodiment, are sufficiently close in diameter to the diameter of teeth 20 so that there is a frictional fit during their engagement to avoid the need for glue, screws etc. A complete view of combined upper and lower housings 78 and 76 of guide aperture 60 as well as the guide aperture's 60 fixed position within support assembly 28 is shown in FIG. 7.

Figure 10:
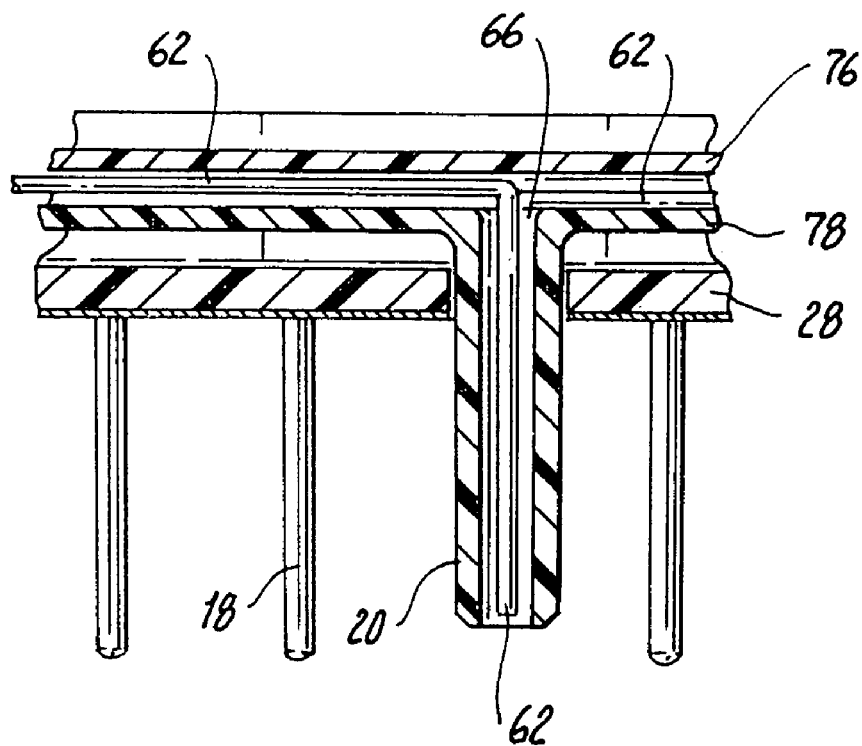
FIG. 10 shows, in an enlarged view, a side-cutaway of a portion of the teeth of the device and the path of an optical cables through the guide aperture and tooth.

Referring to FIG. 10, an enlarged side cutaway view of a portion of teeth 18 and 20, guide aperture 60 and support assembly 28 is shown in relationship to optical cables 62. In this view, the 90° bend in optical cable 62 and its extension through orifice 66 and tooth 20 is shown. Respective upper and lower housing 76 and 78 of guide aperture 60 are shown forming a cavity through which optical cable 62 is guided. As mentioned above, a plurality of optical cables 62 is aligned, engaged and secured with each guide groove 64 and preferably an optical cable 62 is provided for each guide groove 64 such that each orifice 66 and tooth 20 aligned with a respective guide groove 64 can receive an optical cable 62.

Figure 9:
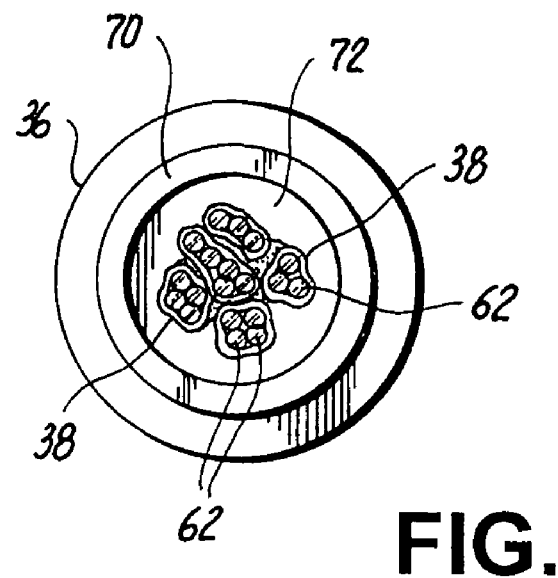
FIG. 9 is a cross-section of the coupling assembly, guide cables and optical cables taken along the line 9—9 in FIG. 7.

Optical cables 62 are configured to convey a portion of the laser beam output of laser source 30 outward from hair treatment device 10. Referring to FIG. 7, coupling assembly 36 aligns first ends of guide cables 38 with laser source 30 thereby coupling and aligning the first ends of optical cables 62 housed within laser source 30. FIG. 9 shows a cross section of coupling assembly 36 taken along the line 9—9 in FIG. 7. As shown, coupling assembly 36 is configured to retain the first ends of guide cables 38 such that first ends of the optical cables 62 can couple a portion of the laser beam output by laser source 30 for transmission to a remote end disposed within a tooth 20. The arrangement of optical cables 62 and coupling assembly 36 allows for the use of a single laser source 30. Additionally, using a single laser source 30 has the benefit that each separate beam part received by optical cables 62 can have substantially the same amount of energy. This avoids the situation which could happen if multiple laser sources were used to generate individual beams, because a multiple laser system can produce hot spots due to discrepancies in the output power produced by individual lasers.

Figure 11B:
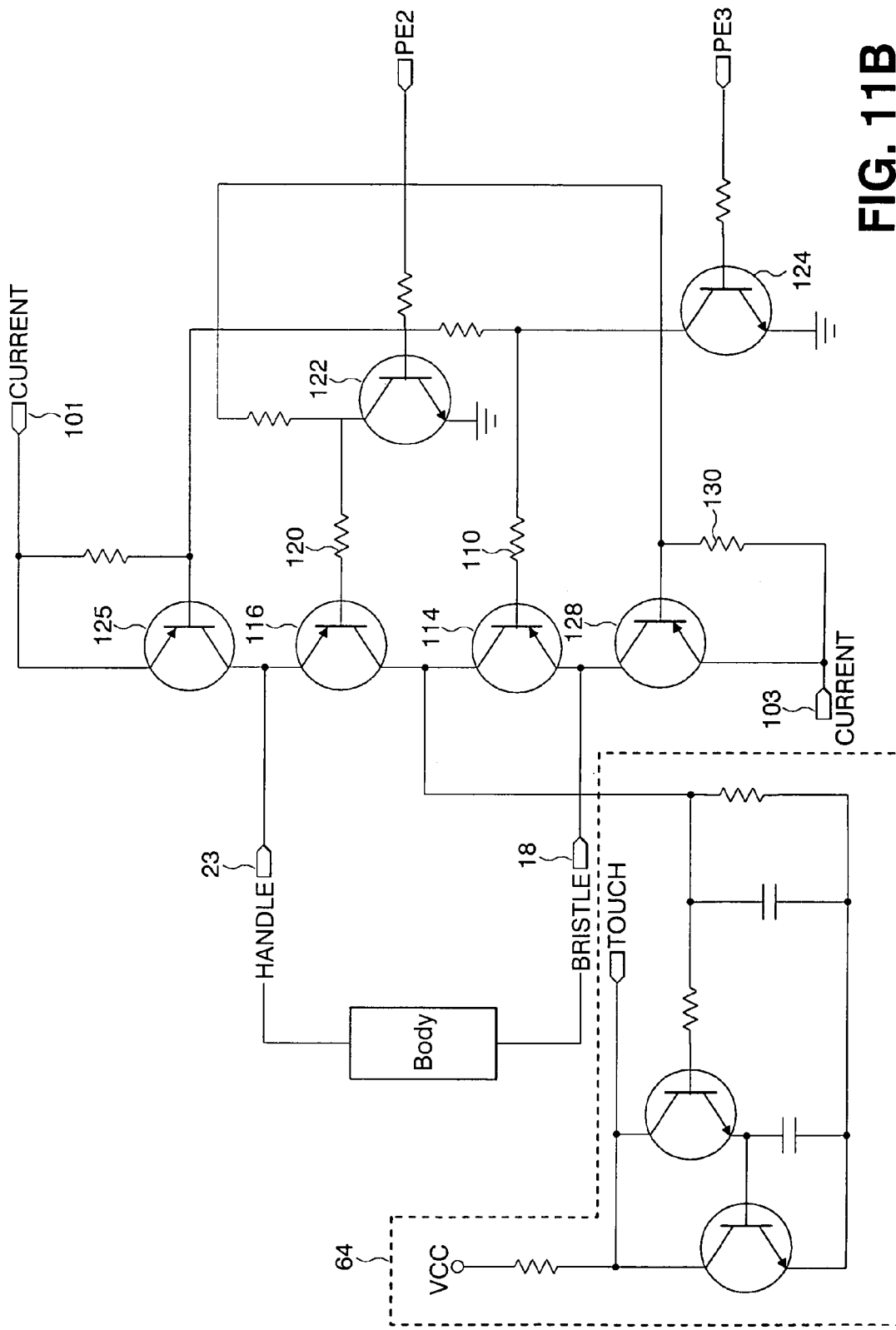
Figure 11C:
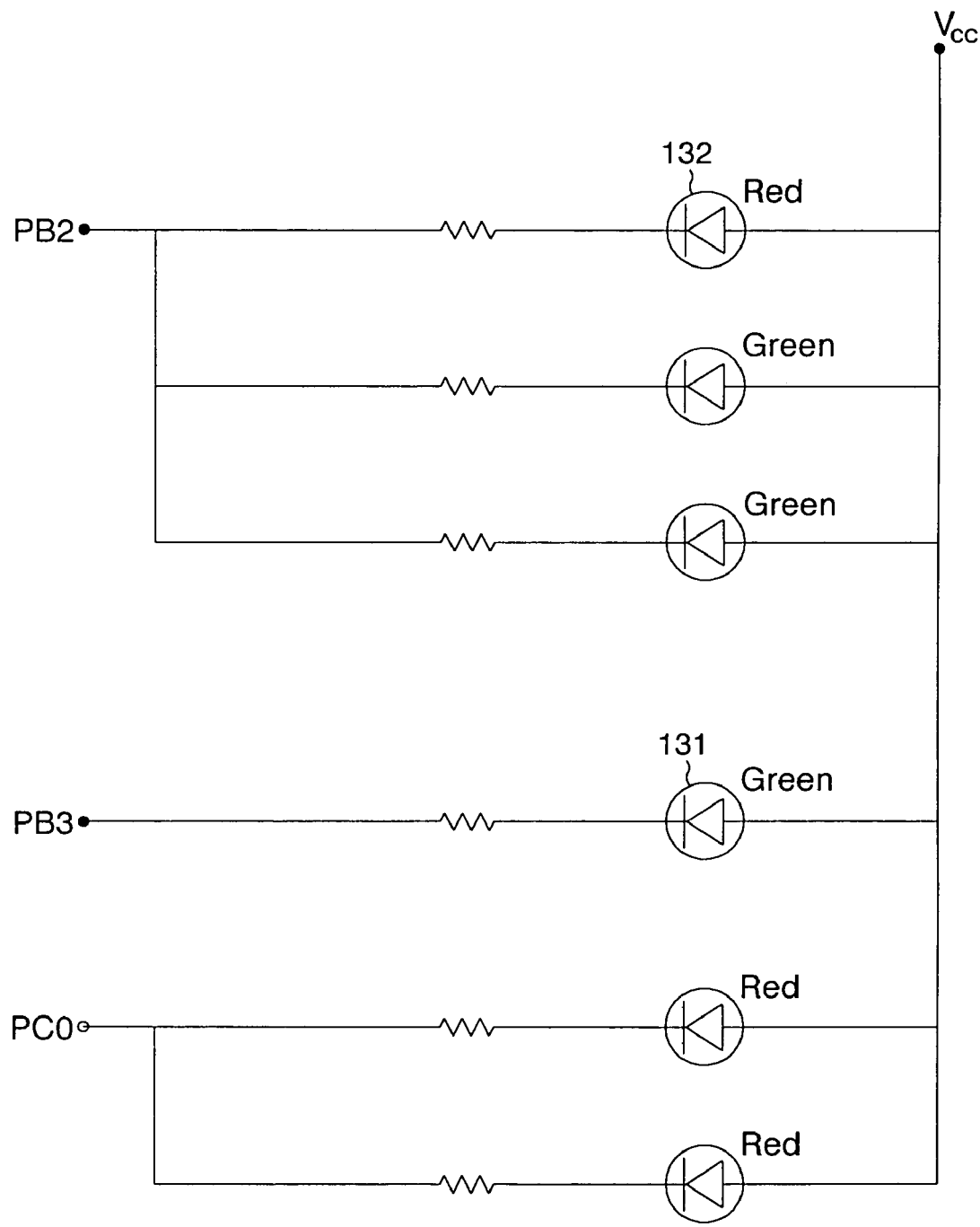

Referring to FIG. 6, PCB 42 includes a microcontroller 43 mounted thereon, for interfacing with the electronic circuitry of PCBs 42 and 34 and controlling various components of treatment device 10, such as laser source 30, resonator or oscillator 32, and indication light 14. FIGS. 11A–11B show the electronic circuit diagram of PCBs 42 and 34 with major sections of the circuitry enclosed in dashed-dot blocks. Resonator 32 is secured to upper housing 22 and connected to PCB 34. PCB 34 can control the output of resonator 32 including turning it on during activation of treatment device 10, during galvanic and laser treatment modes or at predetermined intervals during treatment.

With reference to FIG. 11A, several components of the electronic circuitry are described, including a laser diode 135, a buzzer 44 and green and red LEDs, 131 and 132, respectively. In a particular implementation, and with reference to FIG. 11A, microcontroller 43 is an NT66P22 microcontroller manufactured by NTK of Taiwan, however any microcontroller providing similar functions to that discussed below may generally be used.

According to the preferred embodiment, buzzer 44 may be a piezoelectric element or conventional vibrating member as used in cellular telephones, for example. The buzzer 44 can be activated through signals between pins PD2 and PD3 of microcontroller 43 at predetermined intervals during the operation of treatment device 10. According to the preferred embodiment, microcontroller 43 activates buzzer 44 at 5, 10 and 15 minute intervals during continuous operation of treatment device 10. Of course, a buzzer need not be provided in a given embodiment. LEDs 130 and 131 are controlled by microcontroller 43 by a driving circuit completed through pins PB2 and PB3 and are activated or deactivated depending on the mode being implemented.

Block 166 includes circuitry for enabling laser mode, including two phases, each phase providing laser diode 135 with a different constant current. Transistors 140 and 141 are controlled by microcontroller 43 which provides base or gate driving signals through pins PF1 and PA2 respectively. When laser mode is activated, microcontroller 43 only turns on either transistor 140 or transistor 141, but not both, at any single given time. Microcontroller 43 drives pin PF1 to turn on transistor 141 and pin PA2 to turn on transistor 140.

During phase 1, microcontroller 43 drives pin PA2, thereby supplying current to resistor 136 and turning on transistor 140. When transistor 140 is turned on, transistor 143 is subsequently turned on and current flowing from the emitter of transistor 143 drives laser diode 135. As a result, a constant current flows through laser diode 135, the value of which will be dependent on the initial driving current microcontroller 43 supplies to pin PA2. Likewise, in phase 2, microcontroller 43 drives pin PF1 and not pin PA2, thereby supplying current to resistor 138 and turning on transistor 141. When transistor 141 is turned on, transistor 143 is subsequently turned on and current flowing from the emitter of transistor 143 can turn on laser diode 135. Similarly to phase 1, this constant emitter current drives laser diode 135, however in this instance the amount of current driving laser diode 135 will be dependent on the initial driving current microcontroller 43 supplies to pin PF1 as opposed to pin PA2. According to the preferred embodiment, a constant current of 40 mA flows though laser diode 135 during phase 1 and a constant current of 20 mA flows through laser diode 135 during phase 2. Thus microcontroller 43 controls which of two levels of laser light are output by laser diode 135 which will be transmitted to a user's head via fiber optics.

FIG. 11B shows the electric circuitry for implementing galvanic mode, including an output polarity switch function for automatically changing the polarity of the applied current in prescribed periods, e.g., every 60 seconds. Transistors 122 and 124 are controlled by microcontroller 43 through pins PE2 and PE3 respectively. When treatment device 10 operates in galvanic mode, microcontroller 43 only turns on either transistor 122 or transistor 124, but not both, at any single given time. Microcontroller 43 sends control signals through pin PE2 to turn on transistor 122, and through pin PE3 to turn on transistor 124.

When transistor 124 is on (conducts), transistor 125 is subsequently turned on and transistor 114 is also turned on by current flowing through resistor 110. Transistors 122, 116 and 128 are off (do not conduct) when transistor 124 is on. When transistors 125 and 114 conduct, current can flow from current source 101 to handle 23, through the user's hand and return through teeth 18 via the user's head. In this case, handle 23 acts as a negative pole and teeth 18 act as a positive pole. Current flows from current source 101 through handle 23, through the user's body, returning through teeth 18. Alternatively, when transistor 122 is turned on, transistor 128 is subsequently turned on and transistor 116 is also turned on by current flowing through resistor 120. When transistor 122 is on, transistors 124, 125 and 114 are off (do not conduct). When transistors 116 and 128 conduct, current can flow from current source 103 to teeth 18, through the user's head and return through handle 23 via the user's hand. In this case, handle 23 acts as a positive pole and teeth 18 act as a negative pole. If in the course of applying treatment device 10 to the user's head contact between teeth 18 and the user's head or between the handle 23 and the user's palm is severed the closed-circuit detection circuitry of block 64 will temporarily hold the completed circuit until contact with these contacts is restored or the passage of a predetermined time-out period (5 seconds or such time permitted by the discharge circuit of block 64) has passed. The time-out interval for treatment device 10 is selected using a combination of resistors and capacitors. One of ordinary skill in the art will realize the advantages of the closed-circuit detection circuitry of block 64 in that treatment device 10 can be configured for use with alternative time-out intervals simply by installing appropriate resistors or capacitors during manufacture of PCB 42.

Treatment device 10 provides three treatment modes of therapy, including galvanic, laser and combined modes. FIGS. 12A, 12B and 12C show flow diagrams of the steps for implementing these modes. The preferred predetermined treatment duration is approximately fifteen minutes including either the galvanic, laser or combined galvanic and laser treatment, however, the treatment duration may be in the general range of about one to fifteen minutes. In a preferred embodiment, the three treatment modes are manually executed sequentially, however, in the alternative, may be automatically executed. During treatment, treatment device 10 continuously monitors whether the button 12 is pressed (steps 402 and 414) and whether the closed state of the circuit path has been interrupted for the greater of a predetermined time-out period (step 412).

Referring to FIG. 12A, when button 12 is pressed, treatment device 10 switches from an active "off" state (off-mode 400) to an active "on" state (galvanic mode 406). A timer is initialized or reset at step 408 to establish a treatment time on the condition that a continuous circuit path is not disrupted for the greater of the predetermined timeout period. In step 410, treatment device 10 is automatically placed in the first of two stages or phases of galvanic treatment mode. Specifically, PCB 42 preferably generates DC 23 Volts, outputs a preferably constant current of about 0.1 mA to handle 23 and teeth 18 via wires 56 and 54, respectively, preferably changes the polarity of the current every 60 seconds, and can turn red LED on to indicate active-galvanic treatment status. At step 412, a test for a continuous circuit path is tested where the continuous circuit path is defined between handle 23, user 4, teeth 18 and PCB 42. If the closed circuit is disrupted (e.g., contact between user 4 and teeth 18 is broken) for the greater of the predetermined timeout period (e.g., 5 seconds) treatment device 10 will timeout and microcontroller 43 will put the device into off mode. If timeout does not occur, microcontroller 43 can activate buzzer 44, say, every five minutes until the treatment device either times out (step 412) or the a keypress is detected at step 414 signifying a change from galvanic to laser mode.

According to the preferred embodiment, microcontroller 43 drives buzzer 44 for two long beeps 420 when first five minutes of operation is detected at 418, three long beeps 428 when ten minutes of operation detected at step 426 and four long beeps 432 when the complete fifteen minute treatment time is detected at step 430. As shown, after five and ten minutes of operation are detected at steps 418 and 426, respectively, microcontroller 43 drives buzzer 44 for the appropriate number of beeps, 420 or 428, and checks for a time-out 412 or keypress 414 condition. In the event the closed circuit path is disrupted for the greater of a predetermined timeout interval, the timeout condition is triggered at 412 and treatment device 10 switches to off mode 400. Referring to step 430, when the timer reaches fifteen minutes, microcontroller 43 drives buzzer 44 to sound four long beeps 432, after which treatment device 10 has reached the full treatment time and switches to off-mode.

This first treatment phase is intended to help cleanse the scalp and hair follicles. As discussed further detail below, this phase is particularly designed to aid the penetration of the active ingredients into the root of the hair follicle to ensure effective hair growth stimulation. During this cleansing stage, the electrodes receive direct current impulses (23 V) of about 0.1 mA and the polarity changes every 60 seconds. While the cleansing stage may last for longer or shorter periods, the preferred method is for this phase to last seven minutes.

Figure 17A:
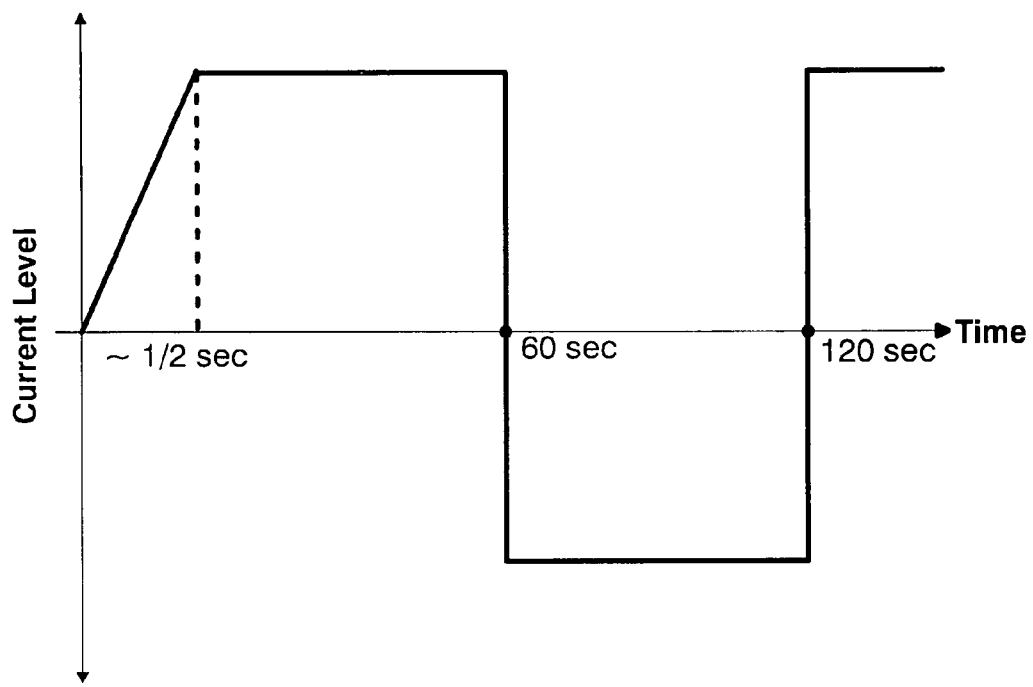
FIG. 17 shows, is a simplified illustration of the features of the waveform of the electrical signal employed for each current treatment phase according to the present invention.

The waveform for the first treatment phase is shown in FIG. 17A. The waveform includes a non-repeating ramp period followed by a level period. The ramp period is preferably ½ second; the level period is preferably 60 seconds. The waveform than changes polarity and repeats at a negative polarity for another 60 seconds. The waveform continues changing the polarity of a constant current every 60 seconds for the remainder of phase 1.

As mentioned above, treatment device 10 is configured to automatically operate in two phases or stages when in galvanic mode. In a preferred embodiment, the two current treatment stages are automatically executed sequentially, without any other intervening treatment modes. Referring to steps 422 and 424, after seven minutes of continuous operation in galvanic mode (operation without time-out), device 10 automatically switches from phase 1 to phase 2. Specifically, when the timer reaches seven minutes, control passes to step 424 and microcontroller 43 switches from a constant 0.1 mA output to a pulsed 0.04 mA output. Thus, less current is output by PCB 42 to handle 23 and teeth 18. As in phase 1 (step 410), red LED remains on and microcontroller 43 continues to change the polarity of the current, however in phase 2 the polarity is changed every 20 seconds as opposed to 60 seconds in phase 1. When treatment device 10 switches to phase 2, the treatment timer is not initialized or reset and thus continues its count. In this case, the microcontroller's 43 operation of buzzer 44 will be unaffected by the transition and will continue to sound at five minute intervals as discussed above.

The second treatment phase is intended to inhibit dihydrotstosterone (DHT) which is a major cause of hair loss and stimulate protein synthesis and cells at the hair follicle level causing the follicle to generate new and healthier hairs. Unlike phase 1, during this current treatment phase, the electrodes receive pulsed direct current impulses of about 0.04 mA having a frequency of between 1 and 10 Hz and a duty cycle of between 30 and 70 percent. Preferably, the impulses are of about 0.04 mA, at a frequency of 3 Hz, and a 50 percent duty cycle. While phase 2 may last for longer or shorter periods, the preferred method is for this stage to last 8 minutes.

Figure 17B:
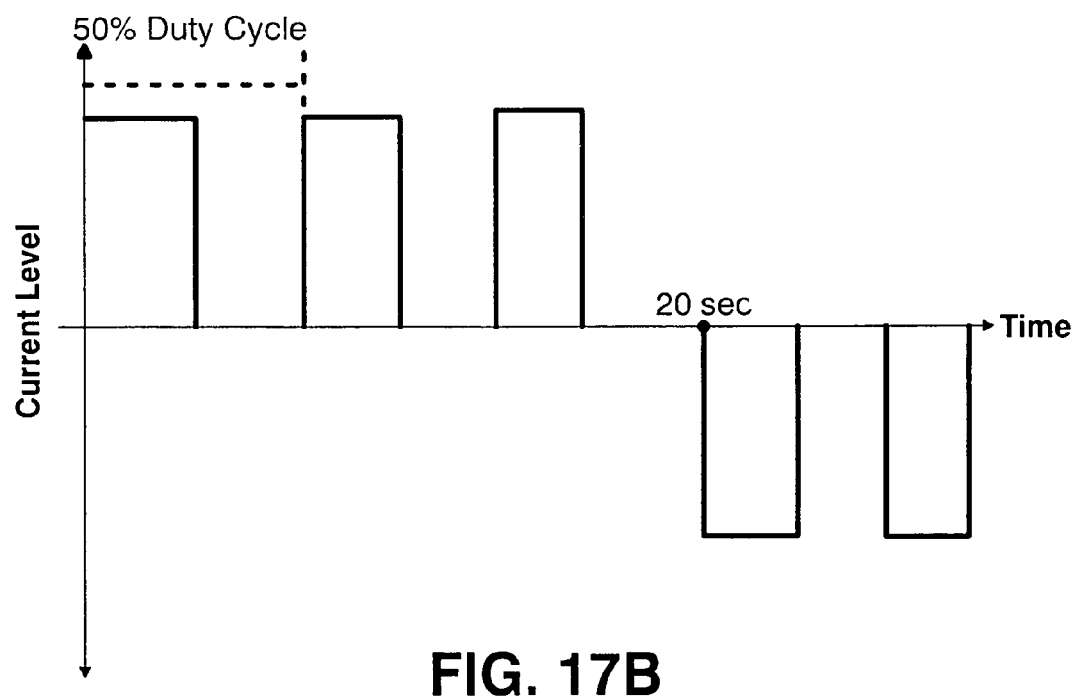

The waveform for the second treatment stage is shown in FIG. 17B. This waveform is a square wave of a particular duty cycle. For the first portion of each period, the waveform is a square wave characterized by a rapid rise to a high current level, a hold at that high current level, followed by a rapid return to near zero current. The second portion of each period is a hold at or near zero current level. The waveform then repeats for the next period. The ratio of time at the high current level to the time period from one rapid rise to the next rapid rise is called the duty cycle. Preferably, the duty cycle is 50 percent, meaning that the two portions are of equal duration. After 20 seconds, the polarity switches and the waveform repeats in the reverse polarity.

When switch 10 is pressed twice consecutively from the off position, or once while operating in galvanic mode, treatment device 10 switches to laser mode at step 416. Referring to step 510 of FIG. 12B, in laser mode, microcontroller 43 turns off transistors 122 and 124 thereby disabling the current sources 101 and 103. Treatment device 10 generates DC 5 Volts with a constant 40 mA current flowing through laser diode 135 (FIG. 11A) and turns red LED 132 off and green LED 131 on. When activated, green LED 131 illuminates a green glow in indication window 20 which signifies to the user that treatment device 10 has left galvanic mode and is currently operating in laser mode. As discussed above regarding the switch from phase 1 to phase 2 in galvanic mode, while switching to laser mode, the timer is not initialized or reset and continues its count. Thus, microcontroller's 54 operation of buzzer 44 will be unaffected by the transition from galvanic to laser mode and will continue to sound at five minute intervals as discussed above. A user can switch treatment device 10 from the galvanic to laser mode at any time during the fifteen minute treatment time, without resetting the timer.

In laser mode, a closed-loop check (timeout check) is carried out at step 512. Similar to the timeout check in galvanic mode, if the closed-loop between the treatment device and the user 4 is broken for more than the predetermined timeout period of five seconds, the treatment device will go into off-mode, e.g., by turning off the drive transistors 140, 141. If the device does not timeout at step 512, microcontroller 43 will continue to sound buzzer 44 at five minute intervals until the treatment device either times out (step 512) or the a keypress is detected at step 514 signifying a change from laser to combined galvanic and laser mode.

As discussed above, buzzer 44 sounds two long beeps 520 when five minutes of operation is reached as detected at 518, three long beeps 528 when ten minutes of operation is reached as detected at step 526 and four long beeps 532 when the complete fifteen minute treatment time is reached as detected at step 530. As shown, when five and ten minutes of operation are detected at steps 518 and 526, respectively, microcontroller 43 drives buzzer 44 for the appropriate number of beeps (step 520 or step 528) and checks for a time-out condition 512 or keypress condition 514. Referring to step 530, when the timer reaches fifteen minutes microcontroller 43 drives buzzer 44 to sound four long beeps 532, after which treatment is complete and treatment device 10 switches to off-mode 500.

After the first seven minutes of continuous operation in laser mode (operation without time-out), device 10 automatically switches from phase 1 to phase 2 (step 524). When the timer is detected having reached seven minutes at step 522, control passes to step 524 and microcontroller 43 switches from a constant 40 mA output to a 20 mA output. As in phase 1 (step 510), microcontroller 43 continues to the red LED. While switching to phase 2, the treatment timer is not initialized or reset and thus continues its count. Accordingly, the microcontroller's 54 operation of buzzer 44 will be unaffected by the transition and will continue to sound at five minute intervals as discussed above.

Referring to FIG. 12C, when switch 10 is pressed three consecutive times from the off position, twice from galvanic mode or once from the laser mode, device 10 switches from laser mode to combined mode. In combined mode both galvanic and laser treatments are applied, preferably with both treatments occurring simultaneously. Referring to step 610, microcontroller 43 generates DC 23 Volts and outputs a constant 0.1 mA current to handle 23 and teeth 18 via wires 56 and 54, respectively, automatically changes the polarity of the current every 60 seconds and generates DC 5 Volts with a constant 40 mA current flowing through laser diode 135 (FIG. 11A) and turns both green and red LEDs 131 and 132 on. The combined activation of both the red and green LEDs illuminates a red/green glow in indication window 20 which signifies to the user that treatment device 10 has left laser mode and is currently operating in combined mode. As discussed above regarding the switch from phase 1 to phase 2 in the galvanic and laser modes, the timer is not initialized or reset and continues its count throughout mode changes. Thus, the treatment time and five-minute buzzer outputs can be held constant regardless of when a mode change occurs.

In combined mode, a continuous closed-loop check (timeout check) is carried out at step 612. Timeout check 612 is the same check preformed in galvanic and laser modes. Namely, as discussed above, if the closed-loop between first and second conductive surfaces of treatment device 10 and the user's head and hand is broken for more than the predetermined timeout period of five seconds, the treatment device will go into off-mode. If treatment device 10 does not timeout, microcontroller 43 will continue to sound buzzer 44 at five minute intervals until the treatment device either times out (step 612) or the a keypress is detected at step 614 signifying a change from combined galvanic and laser mode to off-mode.

As discussed above, buzzer 44 sounds two long beeps 620 when five minutes of operation is reached as detected at 618, three long beeps 628 when ten minutes of operation is reached as detected at step 626 and four long beeps 632 when the complete fifteen minute treatment time is reached as detected at step 630. As shown, after the first five and ten minutes of operation are detected at steps 618 and 626, respectively, microcontroller 43 drives buzzer 44 for the appropriate number of beeps (620 or 628) and checks for a time-out condition 612 or keypress condition 614. Referring to step 630, when the timer reaches fifteen minutes microcontroller 43 drives buzzer 44 to sound four long beeps 632, after which treatment is complete and treatment device 10 switches to off-mode 600.

After the first seven minutes of continuous operation in combined mode (operation without time-out), device 10 automatically switches from phase 1 to phase 2 (step 624). Specifically, when the timer reaches 7 minutes as detected at step 622, control passes to step 624 and microcontroller 43 switches from a constant 0.1 mA current flowing through galvanic current generator 4 to a pulsed 0.04 mA current. Microcontroller 43 also switches from a constant 40 mA current flowing through laser diode 135 to a 20 mA constant current. As in phase 1 (step 610), microcontroller 43 continues to drive both green and red LEDs, 131 and 132, respectively, signifying that the device is still in combined mode. During the treatment device's 10 switch into phase 2, the treatment timer is not initialized or reset and thus continues its count. Accordingly, the microcontroller's 43 operation of buzzer 44 will be unaffected by the transition and will continue to sound at five minute intervals as discussed above. Once in combined mode, any additional press of button 12 will cause treatment device 10 to enter off mode.

If the user fails to properly hold the treatment device 10 to the head or hair, thereby disrupting the closed circuit, the device 10 will enter off mode after a predetermined time-out period. The preferred predetermined time out interval is approximately five seconds; however, the interval may generally be in the range of about five to fifteen seconds. The purpose of having an automatic time out is to conserve power when the treatment device 10 is not in use and to thereby avoid having to replace the battery too frequently.

When the closed circuit path is maintained, the device 10 automatically cycles through two galvanic current treatment phases, each phase classified by the amount of current microcontroller 42 supplies to the user's head via the first and second conductive surfaces, teeth 18 and handle 23. In the preferred embodiment described above, the phase 1 current level is approximately 0.1 mA (milliamp or a thousandth of an amp) and the phase 2 current level is approximately 0.04 mA. However, these current levels may be continuously varied and may generally be in the range of about 0.01 mA to 0.1 mA. Upon activation of galvanic mode, device 10 will default to operate in phase 1 current level (continuous direct current) until the timeout condition is triggered or, in the event that such contact is maintained, without triggering the timeout condition, device 10 automatically switches to phase 2 current level (pulsed) after reaching a prescribed time-interval.

Figure 13:
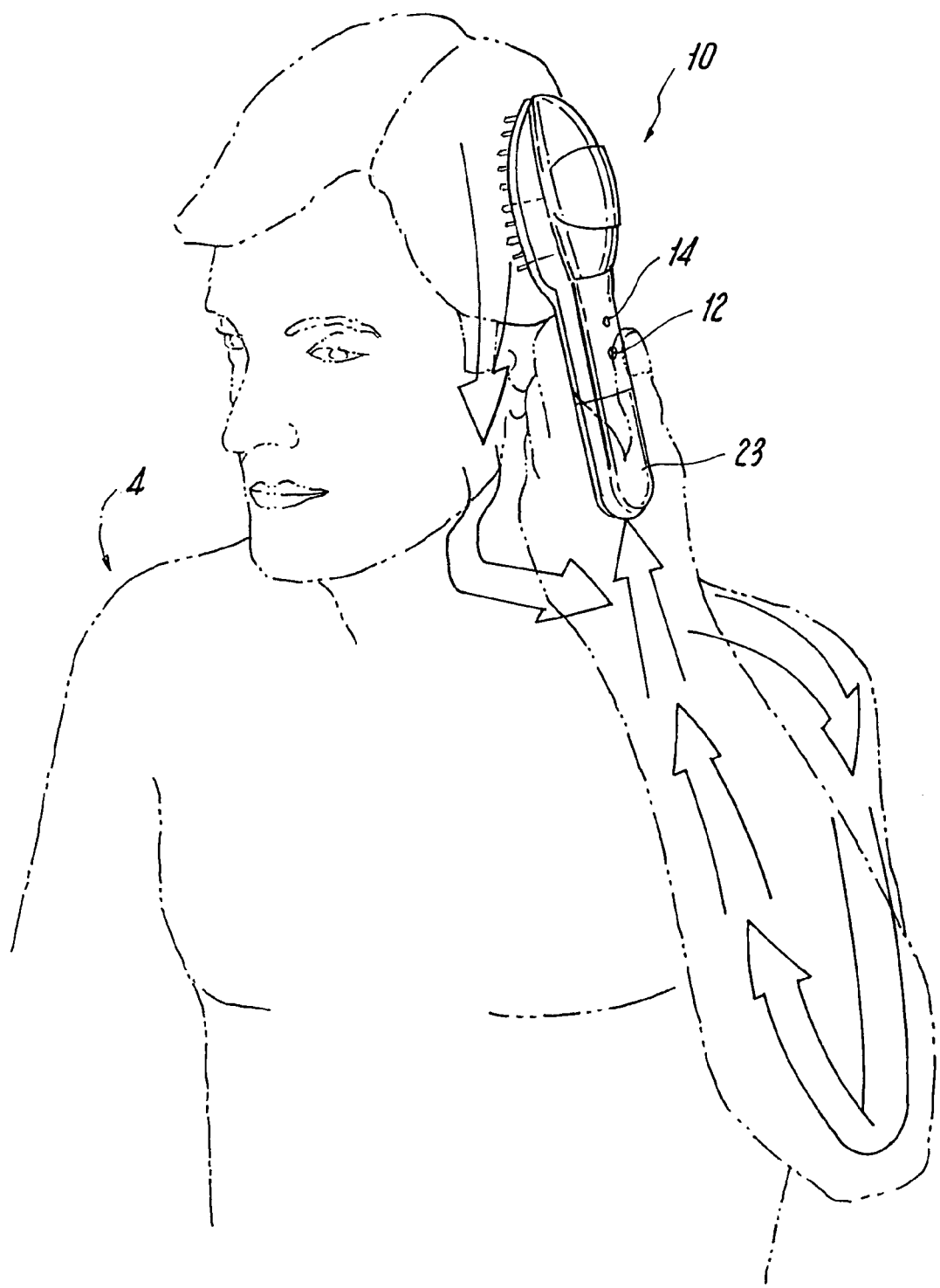
FIG. 13 is a perspective view of the device during treatment, illustrating the direction of current flow and the closed-circuit path in galvanic mode.

Referring to FIG. 13, treatment device 10 is designed to be a self-contained, handheld, device which selectively applies low-amperage galvanic current and low-level laser light to the scalp and/or hair of a user 4. In use, the user draws the teeth of device 10 through his or her hair in the same manner as the user would use a conventional hair comb or brush. FIG. 13 illustrates the path of current from teeth 18 through the user's body and back to handle 23. A first conductive surface is associated with handle 23 and contactable with the user's hand when the treatment device is being held. A second conductive surface is associated with teeth 18, on a head portion of treatment device 10, and is contactable with the user's head when the treatment device is in use. As discussed above with reference to FIG. 6, a circuit path portion is defined among the first conductive surface, the second conductive surface and PCB 42. When treatment device 10 is not in use, this circuit path is in an open state and current does not conduct. However, when the first and second conductive surfaces are simultaneously contacted by user 4, the circuit path is completed generally along the path illustrated in FIG. 13 and PCB 42 can transmit current to the user's scalp through these surfaces. As mentioned above treatment device 10 preferably automatically changes the polarity of applied current every 60 seconds in phase 1 and every 20 seconds in phase. Thus, as the polarity changes, the direction of current flow (the arrows in FIG. 13) will also change. As such, current shown flowing through the user's 4 body from teeth 18 to handle 23 can similarly originate at handle 28 and return at teeth 18. Of course, the device 10 can be constructed to not change polarity of the current, if desired.

Figure 14:
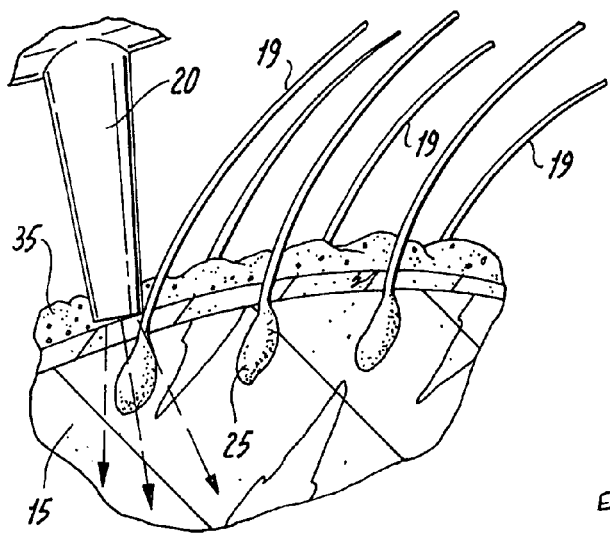
FIG. 14 shows, in an enlarged view, a tooth of the device during the application of laser light to the scalp and hair follicle of the user.

FIG. 14 illustrates a side view of a tooth 20 of device 10 as it is drawn through the user's hair 19 and over his or her scalp 15. As shown, tooth 20 is able to move between and over individual hairs 19, outputting laser light to these hairs and to scalp 15 as it moves through the hair. As shown, laser light output from tooth 20 can penetrate below the surface of hairs 19 and scalp 15 to hair follicles 25.

Figure 15:
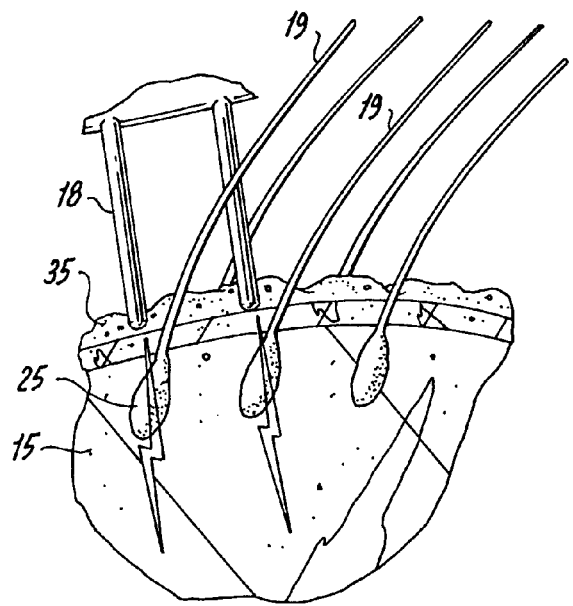
FIG. 15 shows, in an enlarged view, teeth of the device during the application of current to the scalp and hair follicle of the user.

FIG. 15 illustrates a side view of two teeth 18 of device 10 as they are moved through the user's hair 19 and over his or her scalp 15. Like teeth 20, teeth 18 are able to move between or over individual hairs 19 and reach the surface of scalp 15. Contact between teeth 18, scalp 15 and hair 19 allows current output by teeth 18 to enter the user scalp and effect the hair follicles.

Figure 16:
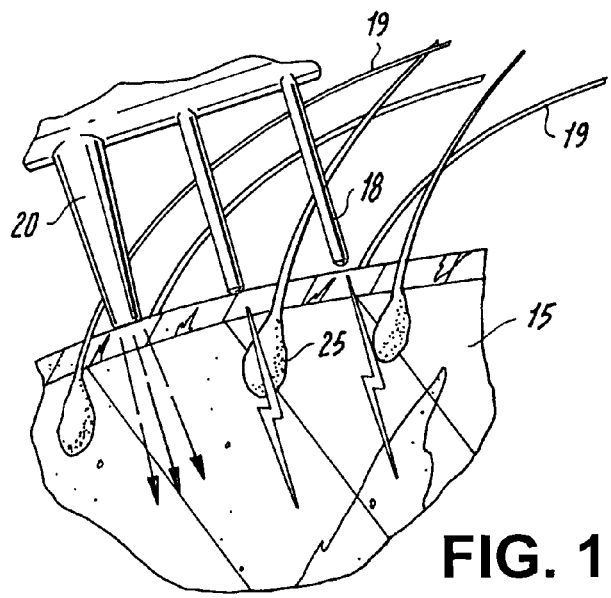
FIG. 16 shows, in an enlarged view, teeth of the device during the application of current and laser light to the scalp and hair follicle of the user.

Referring to FIG. 16, laser light, aligned with and output from teeth 20, and galvanic current, output from teeth 18, are able to reach the scalp and hair follicles as the teeth are combed through the user's hair. Referring to FIGS. 14–16, treatment device 10 provides three treatments modes, including laser (FIG. 14), galvanic (FIG. 15) and combined modes (FIG. 16). In galvanic mode, conductive teeth 18 can be placed in contact with the user's head, hair or scalp and current output by the teeth can flow thereto.

According to a preferred mode of treatment, and with reference to FIG. 14, a galvanic current is used to drive a treatment solution 35 into the hair follicle through a process known as transdermal iontophoresis. Preferably, the treatment solution contains active ingredient Liposterolic Extract of Seronoa Repens which is a natural occurring product, but other solutions such as conductive solutions can be used to assist in the treatment. The application of current to the user's scalp aids penetration of the active ingredient into the root of the hair follicle to ensure effective hair growth stimulation. This ingredient effectively blocks the action of testosterone on the follicle cells two ways: blocking the conversion of testosterone to dihydrotestosterone (DHT) by blocking the action of 5-Alpha reductase and blocking the binding of DHT to the hair follicle cells minimizing the effects of DHT in causing both hair loss and inhibiting hair growth. Excess DHT is the primary cause of 90% of hair loss problems.

Prior to applying treatment solution 35 and putting treatment device 10 in galvanic mode, a user can first clean the hair and scalp portion where the user wishes to apply the treatment and then massage a water-based cleansing mixture of live yeast and bacteria to the hair and scalp portion. This mixture will produce enzymes to clear organic oils and debris from the scalp, help the galvanic and laser light treatments penetrate more effectively and unclog the pores to provide a more assuredly barrier free path for new hair growth. After applying the cleanser to the hair and scalp portion, the user can then apply treatment solution 35 as discussed above, switch treatment device 10 into galvanic mode and comb conductive teeth 18 through the hair or over the scalp portion to be treated such that the teeth contact the hair and/or scalp.

In an alternative embodiment, the galvanic circuit can be completed and the closed-circuit path of a modified treatment device 10 can be tested, by an arrangement which directs the current path more locally, within and confined to the vicinity of the teeth 18. In this arrangement, wire 54 is electrically connected to a first portion of the teeth 18 while wire 56 is electrically connected to a second portion of the teeth 18 rather than to the handle 23. More preferably, the wires 54, 56 are in electrical connection with adjacent or proximate teeth 18 so that contact to the user's head completes the circuit along a short circuit path. This has the effect of keeping current topical, as the two contacting poles are generally parallel and so the current will flow along the skin surface which is the shortest path to the return pole.

Although the present invention has been described in terms of the preferred embodiment above, numerous modifications and/or additions to the above-described preferred embodiments would be readily apparent to one skilled in the art. Thus, by way of example and not of limitation, the predetermined time-out interval is preferably about five seconds; however, the interval may generally be in the range of approximately five to fifteen or even sixty seconds. Furthermore, the predetermined application duration is preferably about fifteen minutes; however, the duration may generally be in the range of approximately one to fifteen minutes. In addition, the preferred phase 1 current level is approximately 0.1 mA (milliamp or a thousandth of an amp) and the preferred phase 2 current level is approximately 0.04 mA. However, these current levels may be continuously varied and may generally be in the range of about 0.01 mA to 0.4 mA. Accordingly, the present invention is not to be limited to the particular mechanical, electrical, or program steps or embodiments as shown the drawings and described in detail hereinabove.

In accordance with alternative salient arrangements of the invention, the method as set forth above may be accomplished with a standardized current flow or an automatically adjustable current flow arrangement.

The treatment device may include a rechargeable battery and exposed recharging terminals for recharging the battery, a recharger assembly including a low voltage power supply and a recharger mount for holding the treatment device in position for recharging, and a stand for mounting the treatment device in a convenient location when it is charged but not in use.

While the invention has been described with reference to several embodiments thereof, the invention is more broadly defined and limited only by the recitations in the claims appended hereto and their legal equivalents.

We claim:

1. A handheld treatment device for use with a user's scalp in one or more modes of treatment, comprising:
   a housing which includes a handle portion and a head portion;
   a current generator disposed within the housing and configured to output a current for passage into the user's scalp in a first mode of treatment, said current being substantially less than 1 Ampere;
   a first conductive surface supported by the handle portion and contactable by a user when the treatment device is being held;
   a second conductive surface associated with the head portion and contactable with the user's scalp when the treatment device is in use;
   a circuit path defined among the first conductive surface, the second conductive surface and the current generator, the circuit path being in a closed state and the current generator outputting the current into hair follicles on the scalp when the handle and scalp portions are simultaneously contacted by the user in the first mode of treatment; and
   a switch connected so as to place the handheld treatment device in one of the first mode of treatment, a second mode of treatment, and a combined first and second mode of treatment.

2. The treatment device as in claim 1, further comprising a control circuit connected to the circuit path and operative to disable the current output of the current generator in response to interruption of the closed state of the circuit path.

3. The treatment device as in claim 2, wherein the first conductive surface acts as a negative pole for the current; and the second conductive surface acts as a positive pole for the current.

4. The treatment device as in claim 2, further comprising at least one of a rigid comb and a bristle brush extending from the head portion.

5. The treatment device as in claim 2, wherein the current is a discrete galvanic ion current.

6. The treatment device as in claim 1, further comprising:
   a laser source disposed within the housing and configured to output a laser beam; and
   a plurality of optical cables disposed within the housing, each optical cable having a first end optically coupled to the laser source so as to convey a portion of the laser beam to a second end of the optical cable, the second ends of the plurality of optical cables being spaced from one another.

7. The treatment device as in claim 6, wherein the first ends of the optical cables are orientated so as to receive a portion of the laser beam output by the laser source.

8. The treatment device as in claim 6, wherein the second ends of the optical cables are oriented so as to direct respective portions of the laser beam outward from the treatment device and toward the user's scalp when the hair treatment device is in use in the second mode of treatment.

9. The treatment device as in claim 6, further comprising a retaining member for retaining the first ends of the optical cables in a position where the ends can receive a portion of the laser beam output by the laser source.

10. The treatment device as in claim 6, further comprising at least one of a rigid comb and a bristle brush extending from the head portion, wherein the second ends of the optical cables are disposed within at least one of the rigid comb and the bristle brush.

11. The treatment device as in claim 1, further comprising:
   plural laser sources disposed within the housing and configured to output respective laser beams; and
   plural optical cables disposed within the housing, each optical cable having a first end optically coupled to a respective laser source so as to convey the laser beam of that laser source a second end of the optical cable, the second ends of the plural optical cables being spaced from one another.

12. The treatment device as in claim 1, wherein the current is one of a continuous direct current or a pulsed current having a frequency of approximately 2–10 Hz.

13. The treatment device as in claim 6, wherein the laser beam has a wavelength in the range of 632 nm to 670 nm.

14. A handheld treatment device having one or more modes of treatment for enhancing the growth of hair, comprising:
   a housing which includes a conductive handle portion and a conductive hair and scalp contacting portion;

a galvanic current generator configured to output a current for passage into the user's scalp in a first mode of treatment, the output being substantially less than 1 Ampere;

a circuit path defined among the handle portion, the hair and scalp contacting portion and the galvanic current generator, the circuit path being in a closed state and the galvanic current generator outputting the current into hair follicles on the scalp when the handle and head are simultaneously contacted by the user in the first mode of treatment;

a control circuit operative to disable the current output of the galvanic current generator in response to interruption of the closed state of the circuit path; and a switch connected so as to place the handheld treatment device in one of the first mode of treatment, a second mode of treatment, and a combined first and second mode of treatment.

15. A handheld current and laser hair-treatment device, comprising:

a housing, said housing having a handle portion including a first conductive surface contactable by a user when the treatment device is being held and having a head portion including a second conductive surface contactable with the user's scalp;

a current generator disposed within the housing and configurable to output a discrete current through the second conductive surface for passage into the user's scalp, said current being substantially less than 1 Ampere;

a circuit path defined among the first conductive surface, the second conductive surface and the current generator, the circuit path being in a closed state and the current generator outputting the current into hair follicles on the scalp in a current treatment mode when the handle portion and the head portion are simultaneously contacted by the user;

a laser source disposed within the housing and configured to output a laser beam proximate to the second conductive surface in a laser treatment mode; and a switch connected to selectively place the device in one of the current treatment mode, the laser treatment mode, and a combined current and laser treatment mode.

16. The treatment device as in claim 15, further comprising a control circuit connected to the circuit path and operative to disable the current output of the current generator in response to interruption of the closed state of the circuit path.

17. The treatment device as in claim 15, further comprising at least one of a rigid comb and a bristle brush extending from the head portion.

18. The hair treatment device of claim 15, further comprising a plurality of optical cables disposed within the housing, each optical cable having a first end optically coupled to the laser so as to convey a portion of the laser beam to a second end of the optical cable, the second ends of the plurality of optical cables being spaced from one another.

19. The treatment device as in claim 18, further comprising at least one of a rigid comb and a bristle brush extending from the head portion, wherein the second ends of the optical cables are disposed within at least one of the rigid comb and the bristle brush.

20. The treatment device as in claim 15, further comprising a control circuit connected between the switch, the laser source and the current generator, wherein the control circuit is operable to detect activation of the switch and in response thereto activate or deactivate the laser source and current generator.

* * * * *